US009737562B2

(12) United States Patent
Meloni et al.

(10) Patent No.: US 9,737,562 B2
(45) Date of Patent: Aug. 22, 2017

(54) XENON AND/OR ARGON TREATMENT AS AN ADJUNCT TO PSYCHOTHERAPY FOR PSYCHIATRIC DISORDERS

(71) Applicant: THE MCLEAN HOSPITAL CORPORATION, Belmont, MA (US)

(72) Inventors: Edward G. Meloni, Needham, MA (US); Marc J. Kaufman, Cambridge, MA (US)

(73) Assignee: THE MCLEAN HOSPITAL CORPORATION, Belmont, MA (US)

( * ) Notice: Subject to any disclaimer, the term of this patent is extended or adjusted under 35 U.S.C. 154(b) by 0 days.

(21) Appl. No.: 14/650,479

(22) PCT Filed: Dec. 10, 2013

(86) PCT No.: PCT/US2013/074007
§ 371 (c)(1),
(2) Date: Jun. 8, 2015

(87) PCT Pub. No.: WO2014/093277
PCT Pub. Date: Jun. 19, 2014

(65) Prior Publication Data
US 2015/0306136 A1 Oct. 29, 2015

Related U.S. Application Data

(60) Provisional application No. 61/735,700, filed on Dec. 11, 2012, provisional application No. 61/815,363, filed on Apr. 24, 2013.

(51) Int. Cl.
| | | |
|---|---|---|
| *A01N 59/00* | (2006.01) |
| *A61K 33/00* | (2006.01) |
| *A61K 33/36* | (2006.01) |
| *A61M 16/12* | (2006.01) |
| *A61K 9/00* | (2006.01) |
| *B82Y 5/00* | (2011.01) |
| *A61F 9/02* | (2006.01) |
| *A61M 16/06* | (2006.01) |
| *A61M 16/22* | (2006.01) |
| *A61M 21/00* | (2006.01) |
| *A61M 16/08* | (2006.01) |

(52) U.S. Cl.
CPC ............ *A61K 33/00* (2013.01); *A61K 9/0048* (2013.01); *A61K 33/36* (2013.01); *A61M 16/12* (2013.01); *A61F 9/029* (2013.01); *A61M 16/06* (2013.01); *A61M 16/0891* (2014.02); *A61M 16/22* (2013.01); *A61M 21/00* (2013.01); *A61M 2202/0208* (2013.01); *A61M 2202/0266* (2013.01); *A61M 2202/0291* (2013.01); *A61M 2205/502* (2013.01); *A61M 2210/0612* (2013.01); *A61M 2250/00* (2013.01); *B82Y 5/00* (2013.01)

(58) Field of Classification Search
USPC .......................................................... 424/600
See application file for complete search history.

(56) References Cited

U.S. PATENT DOCUMENTS

| | | |
|---|---|---|
| 4,354,488 A | 10/1982 | Bartos |
| 4,660,555 A | 4/1987 | Payton |
| 4,721,060 A | 1/1988 | Cannon et al. |
| 4,742,824 A | 5/1988 | Payton et al. |
| 5,243,971 A | 9/1993 | Sullivan et al. |
| 5,348,000 A | 9/1994 | Teves |
| 5,413,095 A | 5/1995 | Weaver |
| 6,112,746 A | 9/2000 | Kwok et al. |
| 6,125,844 A | 10/2000 | Samiotes |
| 6,247,470 B1 | 6/2001 | Ketchedjian |
| 6,408,853 B1 | 6/2002 | Chang |
| 6,439,235 B1 | 8/2002 | Larquet et al. |
| 6,595,215 B2 | 7/2003 | Wood |
| 6,715,485 B1 | 4/2004 | Djupesland |
| 6,779,521 B1 | 8/2004 | Schmehl et al. |
| 6,807,966 B2 | 10/2004 | Wright |
| 6,981,502 B2 | 1/2006 | McCormick et al. |
| 7,000,611 B2 | 2/2006 | Klemperer |
| 7,207,333 B2 | 4/2007 | Tohara |
| 7,775,208 B2 | 8/2010 | Carepa et al. |
| 7,866,320 B2 | 1/2011 | Nichols |
| 7,870,860 B2 | 1/2011 | McCormick et al. |
| 2004/0030639 A1 | 2/2004 | Lebda et al. |
| 2004/0204401 A1 | 10/2004 | Migaly |
| 2005/0205098 A1 | 9/2005 | Lampotang et al. |
| 2007/0110821 A1 | 5/2007 | Petzelt |
| 2007/0281925 A1 | 12/2007 | Nielsen |
| 2008/0223369 A1 | 9/2008 | Warren |
| 2009/0181953 A1 | 7/2009 | Mirmehrabi |
| 2009/0252816 A1* | 10/2009 | Abraini ................. A61K 33/00 424/718 |
| 2010/0242959 A1 | 9/2010 | Djupesland et al. |
| 2011/0086107 A1 | 4/2011 | Lemaire et al. |
| 2012/0269906 A1 | 10/2012 | Sheehan |
| 2013/0071487 A1 | 3/2013 | Bessiere et al. |
| 2015/0306136 A1 | 10/2015 | Meloni |

FOREIGN PATENT DOCUMENTS

| | | |
|---|---|---|
| RU | 51501 U1 | 2/2006 |
| RU | 59415 U1 | 12/2006 |

(Continued)

OTHER PUBLICATIONS

Lee (The Journal of Neuroscience, Sep. 27, 2006 • 26(39):10051-10056).*

(Continued)

*Primary Examiner* — Devang Thakor
(74) *Attorney, Agent, or Firm* — Nixon Peabody LLP; David S. Resnick; Teresa A. Ptashka

(57) ABSTRACT

The present invention relates generally to the fields of treating psychiatric disorders, in particular, anxiety disorders including post-traumatic stress disorder (PTSD) in subjects, e.g., human subjects, by administering a xenon and/or argon containing composition. Treatments can also employ psychotherapy in combination with administration of xenon and/or argon, alone or in combination with additional psychotherapeutic medications to treat the anxiety disorder and reduce a symptom of the anxiety disorder in the subject.

10 Claims, 6 Drawing Sheets

(56) References Cited

FOREIGN PATENT DOCUMENTS

| WO | 03060590 A2 | 7/2003 |
|---|---|---|
| WO | 2011146726 A1 | 11/2011 |

OTHER PUBLICATIONS

Haseneder (European Journal of Pharmacology 619 (2009) 33-37).*
Giller (AJNR 11:177-182, Jan./Feb. 1990).*
Orr (Journal of Affective Disorders 61 (2000) 225-240).*
Alkire et al., PNAS, 105(5):1722-1727 (2008). "Neuroimaging analysis of an anesthetic gas that blocks human emotional memory."
International Search Report for PCT/US13/74007 Sent Apr. 17, 2014.
Almonte et al., "Learning and memory deficits in mice lacking protease activated receptor-1", Neurobiol Learn Mem. (2007). 88(3):295-304.
Bantel et al., "Noble Gas Xenon Is a Novel Adenosine Triphosphate-sensitive Potassium Channel Opener", Anesthesiology 112(3):623-630 (2010).
Betourne et al., "Involvement of hippocampal CA3 K(ATP) channels in contextual memory", Neuropharmacology, (2009). 56(3):615-625.
Caldarone et al., "Fear conditioning and latent inhibition in mice lacking the high affinity subclass of nicotinic acetylcholine receptors in the brain", Neuropharmacology, 39(13):2779-2784 (2000).
Daniels et al., "Post-synaptic inhibitory mechanisms of anaesthesia; glycine receptors", Toxicology Letters, 100-101:71-76 (1998).
David et al., "Xenon is an inhibitor of tissue-plasminogen activator: adverse and beneficial effects in a rat model of thromboembolic stroke", Journal of Cerebral Blood Flow & Metabolism, 30(4):718-728. (2010).
Dickinson et al., "Competitive Inhibition at the Glycine Site of the N-Methyl-D-aspartate Receptor by the Anesthetics Xenon and Isoflurane", Anesthesiology, 107(5):756-767 (2007).
Dinse et al., "Xenon reduces glutamate-, AMPA-, and kainate-induced membrane currents in cortical neurones", British Journal of Anaesthesia, 94(4):479-485 (2005).
Feyder et al., "Impaired associative fear learning in mice with complete loss or haploinsufficiency of AMPA GluR1 receptors", Frontiers in Behavioral Neuroscience, 1(4):1-5 (2007).
Haghighi et al., "In a double-blind, randomized and placebo-controlled trial, adjuvant memantine improved symptoms in inpatients suffering from refractory obsessive-compulsive disorders (OCD)", Psychopharmacology, 228(4):633-640 (2013).
Harmer et al., "5HT(3) antagonism abolishes the emotion potentiated startle effect in humans", Psychopharmacology, 186(1):18-24 (2006).
Harrell et al., "Improvements in Hippocampal-Dependent Learning and Decremental Attention in 5-HT(3) Receptor Overexpressing Mice", Learn Mem., 10(5):410-419 (2003).
Haseneder et al., "Xenon Reduces N-methyl-D-Aspartate and Alpha-Amino-3-hydroxy-5-methyl-4-isoxazolepropionic Acid Receptor-mediated Synaptic Transmission in the Amygdala", Anesthesiology, 109 (6):998-1006 (2008).
Haseneder et al., "Xenon Attenuates Excitatory Synaptic Transmission in the Rodent Prefrontal Cortex and Spinal Cord Dorsal Horn", Anesthesiology, 111(6):1297-1307 (2009).
Humeau et al., "A Pathway-Specific Function for Different AMPA Receptor Subunits in Amygdala Long-Term Potentiation and Fear Conditioning", The Journal of Neuroscience, 27(41):10947-10956 (2007).
Iijima et al., "Effects of agents targeting glutamatergic systems on marble-burying behavior", Neuroscience Letters, 471(2):63-65 (2010).
ISR and Written Opinion, PCT/US2013/074007, dated Apr. 17, 2014 (1-10pp.).
Kratzer et al., "Xenon Attenuates Hippocampal Long-term Potentiation by Diminishing Synaptic and Extrasynaptic N-methyl-D-aspartate Receptor Currents", Anesthesiology, 116(3):673-682 (2012).
Liu et al., "Mechanistic Insights into Xenon Inhibition of NMDA Receptors from MD Simulations." J Phys Chem B., 114 (27):9010-9016 (2010).
Nevins et al., "Antagonists at the Serotonin-3 Receptor Can Reduce the Fear-Potentiated Startle Response in the Rat: Evidence for Different Types of Anxiolytic Activity?", The Journal of Pharmacology and Experimental Therapeutics, 268(1):248-254 (1994).
Norris et al., "Modulation of NR2B-regulated contextual fear in the hippocampus by the tissue plasminogen activator system", PNAS, 104(33):13473-13478 (2007).
Rodrigues et al., "Intra-Amygdala Blockade of the NR2B Subunit of the NMDA Receptor Disrupts the Acquisition But Not the Expression of Fear Conditioning", The Journal of Neuroscience, 21(17):6889-6896 (2001).
Rodriguez et al., "Randomized Controlled Crossover Trial of Ketamine in Obsessive-Compulsive Disorder: Proof-of-Concept", Neuropsychopharmocology, 38(12):2475-2483 (2013).
Semenova et al., "Mice Lacking the β4 Subunit of the Nicotinic Acetylcholine Receptor Show Memory Deficits, Altered Anxiety- and Depression-Like Behavior, and Diminished Nicotine-Induced Analgesia", Nicotine & Tobacco Research, 14(11):1346-1355 (2012).
Soltani et al., "A double-blind, placebo-controlled pilot study of ondansetron for patients with obsessive-compulsive disorder", Hum. Psychopharmacol. Clin. Exp., 25(6):509-513 (2010).
Stewart et al., "A Single-Blinded Case-Control Study of Memantine in Severe Obsessive-Compulsive Disorder", Journal of Clinical Psychopharmacology, 30(1):34-39 (2010).
Suzuki et al., "Nitrous Oxide and Xenon Inhibit the Human (alpha 7)5 Nicotinic Acetylcholine Receptor Expressed in Xenopus Oocyte", Anesth. Analg., 96(2):443-448 (2003).
Suzuki et al., "The Diverse Actions of Volatile and Gaseous Anesthetics on Human-cloned 5-Hydroxytryptamine3 Receptors Expressed in Xenopus Oocytes", Anesthesiology 96(3):699-704 (2002).
Tarabrina, Practicum on Post-Traumatic Stress Psychology, Part 1. Chapter 7, Piter Publishing House, St. Petersburg, Russia, 98-101 (2001).
Walker et al., "Amygdala infusions of an NR2B-selective or an NR2A-preferring NMDA receptor antagonist differentially influence fear conditioning and expression in the fear-potentiated startle test", Learn Mem., 15(2):67-74 (2008).
Weigt et al., "Xenon blocks AMPA and NMDA receptor channels by different mechanisms." Acta Neurobiol. Exp., 69 (4):429-440 (2009).
Yamakura et al., "Effects of Gaseous Anesthetics Nitrous Oxide and Xenon on Ligand-gated Ion Channels", Anesthesiology, 93(4):1095-1101 (2000).
David et al., "Modulation by the noble gas argon of the catalytic and thrombolytic efficiency of tissue plasminogen activator", Nuanyn-Schmiedebergs Arch Pharmacol, 386(1): 91-95 (2013).
David et al., "Ex Vivo and In Vivo Neuroprotection Induced by Argon When Given after an Excitotoxic or Ischemic Insult", PLosOne, 7(2):e30934 (2012).
Debiec et al., "Memory Reconsolidation Processes and Post-traumatic Stress Disorder: Promises and Challenges of Translational Research", Biol Psychiatry, 71:284-285 (2012).
Jawad et al., "Neuroprotection (and lack of neuroprotection) afforded by a series of noble gases in an in vitro model of neuronal injury", Neuroscience Letters, 460(3):232-236 (2009).
Johansen et al., "Molecular Mechanisms of Fear Learning and Memory", Cell, 147:509-524 (2011).
Ryang et al.,"Neuroprotective effects of argon in an in vivo model of transient middle cerebral artery occlusion in rats", Crit Care Med, 39(6):1448-1453 (2011).
Zhuang et al., "The protective profile of argon, helium, and xenon in a model of neonatal asphyxia in rats", Crit Care Med, 40(6):1724-1730 (2012).

(56) References Cited

OTHER PUBLICATIONS

Mattusch et al., "Impact of Hyperpolarization-activated, Cyclic Nucleotide-gated Cation Channel Type 2 for the Xenon-mediated Anesthetic Effect: Evidence from in Vitro and in Vivo Experiments", Anesthesiology 122(5) 1047-1059 (2015).

* cited by examiner

XENON AND/OR ARGON TREATMENT AS AN ADJUNCT TO PSYCHOTHERAPY FOR PSYCHIATRIC DISORDERS

CROSS-REFERENCE TO RELATED APPLICATIONS

This application is a 35 U.S.C. §371 National Phase Entry Application of International Application No. PCT/US2013/074007 filed Dec. 10, 2013, which designates the U.S., and which claims benefit under 35 U.S.C. §119(e) of U.S. Provisional Application No. 61/735,700 filed Dec. 11, 2012 and of U.S. Provisional Application No. 61/815,363 filed Apr. 24, 2013, the contents of each of which are incorporated herein by reference in their entireties.

FIELD OF THE INVENTION

This application relates generally to compositions and methods for treating anxiety disorders. Specifically, this application relates to the use of xenon and/or argon alone, or in combination with psychotherapy for the treatment of anxiety disorders, particularly post-traumatic stress disorder.

BACKGROUND OF THE INVENTION

Anxiety Disorders are among the most common mental health disorders, affecting about 40 million American adults age 18 years and older (about 18%) in a given year (Kessler et al. Arch. Gen. Psych 2005). They generally last at least six months and can get worse if not treated. While the cause is not clear, they are believed to have biological, social and psychological components ranging from heredity, personality, life experiences including reactions to stress such as traumatic events, and brain chemistry such as low neurotransmitter levels and problems with amygdala functioning. Anxiety disorders can result in persistent and disabling psychological and physiological symptoms that interfere with the day to day life of an affected individual and include disorders such as acute stress disorder, panic disorder, generalized anxiety disorder, agoraphobia with or without panic disorder, specific phobia, social phobia, obsessive-compulsive disorder, separation anxiety disorder, and post-traumatic stress disorder.

Symptoms of anxiety disorders may vary depending on the disorder, but may include feelings of panic; persistent worry; doubt; dread; fear; uneasiness; uncontrollable, obsessive thoughts; repeated thoughts or flashbacks of traumatic experiences; mood instability; agitation; restlessness; dyspepsia; headaches; dyspnea; nightmares; sleep disturbances; ritualistic behaviors, such as repeated hand washing; insomnia; cold or sweaty hands and/or feet; shortness of breath; palpitations; an inability to be still and calm; intense startle reflex; dry mouth; numbness or tingling in the hands or feet; nausea; muscle tension; and/or dizziness.

Acute stress disorder is a result of a traumatic event in which the person experienced or witnessed an event that involved threatened or actual serious injury or death and responded with intense fear and helplessness. Symptoms include dissociative symptoms such as numbing, detachment, a reduction in awareness of the surroundings, derealization, or depersonalization, re-experiencing of the trauma, avoidance of associated stimuli, and significant anxiety, including irritability, poor concentration, difficulty sleeping, and restlessness. If left untreated, the condition may evolve into Post-traumatic Stress Disorder (PTSD).

Panic Disorder is characterized by sudden attacks of intense fear or anxiety, usually associated with numerous physical symptoms such as heart palpitations, rapid breathing or shortness of breath, blurred vision, dizziness, and racing thoughts. Generalized anxiety disorder is evidenced by general feelings of anxiety such as mild heart palpitations, dizziness, and excessive worry. Agoraphobia is the anxiety of being in places where escape might be difficult or embarrassing or in which help may not be available should a panic attack develop. Phobias result in extreme anxiety and/or fear associated with the object or situation of avoidance. Obsessive compulsive disorders are characterized by persistent, often irrational, and seemingly uncontrollable thoughts and actions which are used to neutralize the obsessions.

PTSD results from experiencing or witnessing a traumatic event that causes intense fear, helplessness or horror. It results in symptoms that fall into three types: re-experiencing the event, emotional numbing and avoidance and hyper-arousal. Repetition of these overwhelming emotions can lead to a cascade of biological events including excessive release of epinephrine and norepinephrine which overpowers the autonomic response leading to clamminess, increased heart rate and breathing, increased blood flow to the muscles and decreased blood flow to the visceral organs. It is currently theorized that this response leads to deep imprinting on the locus coeruleus region of the brain and makes it over sensitized to any further threats (real or imaginary). (Diagnostic and Statistical Manual of Mental Disorders 4th edition (DSM-IV) published by the American Psychiatric Association (APA; Washington, D.C., 1994). PTSD, as that term is used herein, also encompasses the 4 categories of symptoms outlined in the Diagnostic and Statistical Manual of Mental Disorders $5^{th}$ Edition (DSM-V) published by the American Psychiatric Association (APA; Washington, D.C., 2013), which include intrusion (e.g., re-experiencing), avoidance, negative alterations in mood and cognition and alterations in arousal and reactivity. PTSD is also believed to involve the serotonergic and endorphin system. (Holbrook et al, 2010). Experiments have consistently shown a serotonin deficit in "stressed" animals. Through multiple interconnections with the limbic system, serotonin has been found to mediate response to acute and chronic stress, conditioned fear, and flight or fight responses. Further, serotonin also modulates norepinephrine levels thereby leading to indirect effects on stress response through the adrenergic system.

Exposure to traumatic events is common with more than 50% of the US population experiencing one or more traumatic events in their lifetime. (Kessler et al., 1995) However, the rates of PTSD varies according to the population with a lifetime prevalence of approximately 5 to 12% of the population with women having twice the prevalence rate of men (Kessler et al., 1995) and certain segments of the population, such as combat soldiers having rates as high as 25%.

Anxiety disorders are generally treated with a combination of medication and psychotherapy. However, many of the currently prescribed medications merely keep anxiety disorders under control while psychotherapy is attempted, they do not actually treat the disorder. In the case of some disorders, very few medications have been approved. For example, only two medications, sertraline and paroxetine, have been approved by the FDA for treatment of Post-traumatic Stress Disorder. The medications currently used to treat anxiety disorders have unwanted characteristics and side effects including drug interactions, cardiovascular side effects, gastrointestinal side effects, sexual side effects, suicidal ideation and slow onset of action. Even with treatment, residual symptoms and poor functioning continue to be a problem for those suffering from or at risk for anxiety disorders. There is therefore a need in the art for the discovery of additional treatments for anxiety disorders including PTSD.

SUMMARY OF THE INVENTION

The present invention relates to methods, compositions, systems and kits for the treatment of psychiatric disorders by administration of xenon and/or argon gas in combination with psychotherapy. In some embodiments, a xenon and/or argon composition is administered to a subject during and/or after a psychotherapy session to eliminate a high-anxiety response or a symptom of the psychiatric disorder. In some embodiments, a subject self-administers a xenon and/or argon composition as disclosed herein when the subject experiences a traumatic memory or is exposed to a stimulus which provokes a high-anxiety response. In some embodiments, the psychiatric disorder is any psychological and psychiatric disorders, including but not limited to post-traumatic stress disorder (PTSD), acute stress disorder (ASD), panic disorder, obsessive compulsive disorder (OCD), generalized anxiety disorder (GAD), social anxiety disorder, and phobias. In some embodiments, the psychiatric disorder is addiction, e.g., but not limited to, a drug and/or alcohol dependency, an eating disorder (e.g., anorexia or bulimia) etc. In some embodiments, the xenon and/or argon composition is administered to a subject during and/or after a psychotherapy session during a drug craving, or during withdrawal anhedonia. In some embodiments the method encompasses a variety of, or a combination of any of psychotherapy sessions, including but not limited to, cognitive behavioral therapy, psychodynamically oriented treatments, visual reality exposure (VRE) therapy.

As disclosed herein, the inventors have demonstrated herein the consolidation and reconsolidation of traumatic memories in a rodent (e.g., mouse) model in vivo and have demonstrated the memory-altering effects of inhaled xenon gas in rats (male Sprague-Dawley) and have discovered that exposure to xenon (25%) significantly reduces the consolidation of fear memories (FIG. 1). In addition, the inventors have demonstrated that the administration of xenon interferes with memory formation and blocks reconsolidation of traumatic memories. Accordingly, the inventors have demonstrated that xenon administration during, and/or before and/or after a psychotherapy session could be used to reduce fear memories and reduce or "erase" or eliminate untoward memories. In some embodiments, a psychotherapy session is used to reactivate intrusive, or anxiety or emotion-provoking, and/or painful or traumatic memories at which point, such memories would be susceptible to pharmacological disruption with xenon and/or argon given its ability to interfere with neurobiological process involved in memory consolidation (the initial formation of the memory) or reconsolidation ("remembering" the memory)—where the xenon functions to block reconsolidation of the memory.

Accordingly, in some embodiments, the methods of treatment of a psychiatric disorder as disclosed herein encompass administering xenon and/or argon to subjects during and/or immediately after the psychotherapy. In some embodiments, xenon and/or argon can be administered to the subject via gas inhalation using a face and nose mask through which xenon gas would flow. In some embodiments, xenon and/or argon is administered to a subject at a sub-anesthetic dose between 5-50%. In some embodiments, xenon is administered to a subject at a sub-anesthetic dose between 0.5% to 25%. In some embodiments, argon is administered to a subject at a sub-anesthetic dose between 30%-75%. In some embodiments, xenon and/or argon is administered for between 1 minute and 15 minutes, or between 15 minutes and 2 hours. In some embodiments, xenon and/or argon is administered for between 1 minute to 2 hours, for example, between 1 minute and 5 minutes, between 1 min and 10 min, between 1 min and 20 min, between 1 min and 30 min, between 1 min and 40 min, between 1 min and 50 min, between 1 min and 60 min, between 1 min and 90 minutes, or between 1 min and 120 minutes. In some embodiments, a small container of a xenon composition, as described herein, is distributed to a subject who is likely to experience a traumatic event so that it can be self-administered soon after the event, to inhibit consolidation of the memory of that event.

Although the use of xenon to treat psychiatric illnesses has been reported, the use of xenon and/or argon in combination with psychotherapy has not been reported, nor has the use of xenon and/or argon to eliminate or reduce fear-related memories, which would be the practical application for administration of this medication. In fact, the inventors surprisingly discovered that use of xenon significantly reduced conditioned freezing in a rodent model of anxiety (i.e., fear to a specific conditioning context or cue that reminded the animal of the stressor) which did not occur with non-treated animals.

In some embodiments, the xenon composition comprises xenon gas. In some embodiments, the xenon gas is administered (e.g., by inhalation, intraocularly, or intranasally) at a concentration of 10% to 35% by volume in 21% by volume oxygen gas and a balance of nitrogen gas. In some embodiments, the xenon gas is administered at a concentration of 0.5% to 10% by volume in 21% by volume oxygen gas and a balance of nitrogen gas.

In some embodiments, the argon composition comprises argon gas. In some embodiments, the argon gas is administered (e.g., by inhalation, intraocularly, or intranasally) at a concentration of 10% to 35% by volume in 21% by volume oxygen gas and a balance of nitrogen gas. In some embodiments, the argon gas is administered at a concentration of 35% to 75% by volume in 21% by volume oxygen gas and a balance of nitrogen gas.

In some embodiments, the composition comprises a combination of xenon and argon gas.

In some embodiments, the xenon and/or argon composition comprises a nanoparticle or nanosponge. In some embodiments, the nanoparticle or nanosponge is administered intravenously, intraarterially, intramuscularly, subcutaneously, intranasally, or intracranially in any of the method described herein, the xenon composition is administered to the subject over a continuous period of time at least one time per day. In some embodiments, the continuous period of time is at least 15 minutes. In other embodiments, the continuous period of time is at least one minute, at least two minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, or more.

In some embodiments, the subject is administered the xenon and/or argon composition at least one time per day for at least one month.

Also provided are systems for administering a xenon and/or argon gas to the eye of a subject, including: (a)

sealable goggles that cover a subject's eyes that include at least one opening that allows xenon and/or argon gas to enter the space enclosed by the goggles; and (b) a source of xenon and/or argon gas, where the sealable goggles and the xenon and/or argon gas are connected to each other. In some embodiments, the system further includes tubing that connects the sealable goggles to the source of xenon and/or argon gas, a strap for securing the goggles over the subject's eyes, and/or a display screen or a speaker, or both.

One aspect of the present invention relates to a method for treating a subject with a psychiatric disorder comprising administering to the subject a therapeutically effective amount of a xenon and/or argon composition in combination with a session of psychotherapy, wherein during the session of psychotherapy the subject is exposed to a stimulus and trained to develop an altered response to said stimulus. In some embodiments, the psychiatric disorder is selected from the group consisting of a fear and/or anxiety disorder, an addictive disorder, a mood disorder, in some embodiments, the fear and anxiety disorder is selected from the group consisting of: a panic disorder, a phobia, post-traumatic stress disorder (PTSD), social anxiety disorder, obsessive-compulsive disorder (OCD).

In some embodiments, administration of the xenon composition to the subject is during and/or after the session of psychotherapy.

Another aspect of the invention as disclosed herein relates to an improved psychotherapy method comprising administering to a subject in need thereof a therapeutically effective amount of a xenon and/or argon composition in combination with a session of psychotherapy, wherein the xenon and/or argon composition facilities the extinction of a high-anxiety response during the session of psychotherapy, wherein the subject is exposed to a stimulus which provokes a high-anxiety response in the subject during the session of psychotherapy.

Another aspect of the invention as disclosed herein relates to a method for blocking the reconsolidation of re-activated, traumatic memories elicited spontaneously or through the psychotherapy session comprising: (a) administering to the subject a xenon composition; and (b) exposing the subject to stimuli that remind the subject of the event that produces a high-anxiety response or asking the subject to recall or remember details of the traumatic event, phobia, or specific fear. In some embodiments, exposing a subject to a stimuli to remind the subject of an event that produces a high-anxiety response can include, for example, an image, a smell, sound, location, as well as the fear itself (e.g., spiders of a subject with a phobia of spiders, height etc.).

In some embodiments, a psychotherapy session is performed within one hour before the administration of the xenon and/or argon composition, or performed within two hours before the administration of the xenon and/or argon composition.

In some embodiments, a psychotherapy session comprises psychotherapy, for example, but not limited to a psychotherapy session is selected from the group consisting of: exposure-based psychotherapy, cognitive psychotherapy, and psycho-dynamically oriented psychotherapy. In some embodiments, the psychotherapy is aimed at triggering a high-anxiety response or getting the subject to recall or remember details of the traumatic event, phobia, or specific fear.

Another aspect of the present invention relates to a method for blocking the reconsolidation of re-activated, traumatic memories elicited spontaneously in a subject comprising the subject self-administering a therapeutically effective amount of a xenon and/or argon composition after the subject has experienced a memory of a traumatic event, phobia or specific fear, or been exposed to a specific event that produces a high-anxiety response.

In some embodiments, a high anxiety response exacerbates a symptom of a medical disorder selected from the group consisting of: anxiety disorders, chronic pain, neuropathic pain, insomnia and erectile dysfunction, or exacerbates a fear or anxiety disorder, such as, for example, but not limited to a fear or anxiety disorder is selected from the group consisting of: a panic disorder, a phobia, post-traumatic stress disorder (PTSD), social anxiety disorder, obsessive-compulsive disorder (OCD). In some embodiments, a fear or anxiety disorder is post-traumatic stress disorder (PTSD).

In some embodiments, a psychotherapy session comprises: (a) exposing the subject to a stimulus which causes anxiety associated with a medical condition or the post-traumatic stress disorder (PTSD), (b) administering to the subject a therapeutically effective amount of a xenon composition during and/or after the subject is exposed to the stimulus.

In some embodiments, a subject administered a xenon and/or argon composition as disclosed herein has been diagnosed with a fear or anxiety disorder, for example, where the subject has been diagnosed with post-traumatic stress disorder (PTSD). In some embodiments, a subject administered a xenon and/or argon composition as disclosed herein is a human subject. In some embodiments, a subject administered a xenon and/or argon composition as disclosed herein is a domestic animal, such as a dog or horse. In some embodiments of all aspects as disclosed herein, a subject is a war veteran (e.g., human and canine veterans) or any subject who has experienced at least one traumatic event to themselves or been a witness to at least one traumatic event to another. A traumatic event can be any event which results in a bad and undesired memory such as war, explosion, abuse, sexual abuse, rape, an accident (e.g., vehicle accidents, work machinery accidents), a bombing, a shooting and the like.

In some embodiments, the xenon and/or argon composition comprises xenon and/or argon gas, and can be administered, for example, at a concentration of 10% to 35% by volume in 21% by volume oxygen gas and a balance of nitrogen gas. In some embodiments, the xenon gas is administered at a concentration of 0.5% to 10% by volume in 21% by volume oxygen gas and a balance of nitrogen gas. In some embodiments, the argon gas is administered at a concentration of 35% to 75% by volume in 21% by volume oxygen gas and a balance of nitrogen gas. In one embodiment, the concentration of oxygen in the composition is not lower than 21% by volume. In some embodiments, the xenon and/or argon gas is administered by inhalation, intraocularly, or intranasally. In some embodiments, the xenon and/or argon composition comprises a nanoparticle or nanosponge, for example, for intravenous, intraarterial, intramuscular, subcutaneous, intranasal, or intracranial administration of the xenon gas. In some embodiments, the xenon and/or argon gas can be administered by self-administration. In embodiments of self-administration, the xenon and/or argon gas is typically administered intranasally or via inhalation.

In some embodiments, the xenon composition can be administered to the subject over a continuous period of time during and/or after the psychotherapy session, for example, a period of at least 1 minute, at least 2 minutes, at least 5 minutes, at least 10 minutes, at least 15 minutes or more. In some embodiments, a subject is administered the xenon and/or argon composition at least once, or multiple times during the psychotherapy session, for example, at least twice, or at least 3 times or more than 3 times during and/or after the psychotherapy session. In some embodiments, a subject is administered the xenon and/or argon composition after each traumatic memory that the subject wishes to block the reconsolidation of.

In some embodiments, a subject can be administered additional compounds for treatment of the fear or anxiety disorder during or after the psychotherapy session, for example, but not limited to 3,4-methylenedioxy-N-methylamphetamine (MDMA).

In some embodiments, a subject can recall or remember a traumatic event, or experiences a memory of a traumatic event, phobia or specific fear while the subject is asleep. In some embodiments, a subject is exposed to stimuli that reminds the subject of an event that produces a high-anxiety response or asked to recall or remember details of the traumatic event, phobia, or specific fear while the subject is hypnotized.

Another aspect of the present invention relates to a system for administering a xenon and/or argon gas to the eye of a subject, comprising: (a) sealable goggles that cover a subject's eyes that comprise at least one opening that allows xenon and/or argon gas to enter the space enclosed by the goggles; and (b) a source of xenon and/or argon gas, wherein the sealable goggles and the xenon and/or argon gas are connected to each other.

In some embodiments, the system further comprises tubing that connects the sealable goggles to the source of xenon and/or argon gas, where, for example, the sealable goggles further comprise a strap for securing the goggles over the subject's eyes. In some embodiments, the sealable goggles further comprise a display screen or a speaker, or both.

Another aspect provided herein relates to a method for preventing or reducing (e.g., blunting) trauma memory consolidation in a subject, the method comprising administering to a subject in need thereof a therapeutically effective amount of a xenon and/or argon composition during or following a traumatic event (e.g., 1 min, 2 min, 5 min, 10 min, 20 min, 30 min, 45 min, or 60 min following the traumatic event), thereby preventing or reducing trauma memory consolidation in the subject.

Also provided herein are uses of xenon and/or argon compositions alone or in combination with psychotherapy for the treatment of a subject having a psychiatric disorder (e.g., a fear and/or anxiety disorder, an addictive disorder, a mood disorder, among others).

Also provided herein is the use of an argon composition to improve a psychotherapy method. In one embodiment, the argon composition facilitates the extinction of a high-anxiety response during the session of psychotherapy, wherein the subject is exposed to a stimulus which provokes a high-anxiety response in the subject during the session of psychotherapy.

Also provided herein is the use of a xenon and/or argon composition for blocking the reconsolidation of re-activated, traumatic memories elicited spontaneously or through the psychotherapy session. In one embodiment, the subject is exposed to stimuli that reminds the subject of the event that produces a high-anxiety response or asking the subject to recall or remember details of the traumatic event, phobia, or specific fear.

Also provided herein is the use of a self-administered xenon and/or argon composition for blocking the reconsolidation of re-activated traumatic memories elicited spontaneously in a subject after the subject has experienced a memory of a traumatic event, phobia or specific fear, or been exposed to a specific event that produces a high-anxiety response.

Also provided herein are uses of a xenon and/or argon composition for preventing or reducing trauma memory consolidation in a subject.

BRIEF DESCRIPTION OF THE DRAWINGS

FIG. 1A shows one example of an experimental design to test consolidation and reconsolidation of fear memory. FIG. 1B shows data indicating that compared to control animals (Air-treated), Xe-treated rats showed a significant reduction in freezing (a measure of recall of a fear memory) to the context of fear conditioning across test days. FIG. 1C shows data indicating that freezing to the specific conditioning cue (a tone) was also reduced in Xe-treated rats. FIG. 1D shows that 25% xenon blocks reconsolidation of conditioned fear assessed by measuring freezing to context. FIG. 1E shows that 25% xenon blocks reconsolidation of conditioned fear assessed by measuring freezing to tone. FIG. 1F shows that 25% xenon does not block reconsolidation of conditioned fear (assessed by measuring freezing to context) in animals that did not receive a reactivation test. FIG. 1G shows that 25% xenon does not block reconsolidation of conditioned fear (assessed by measuring freezing to tone) in animals that did not receive a reactivation test.

DETAILED DESCRIPTION OF THE INVENTION

Figure 1A:
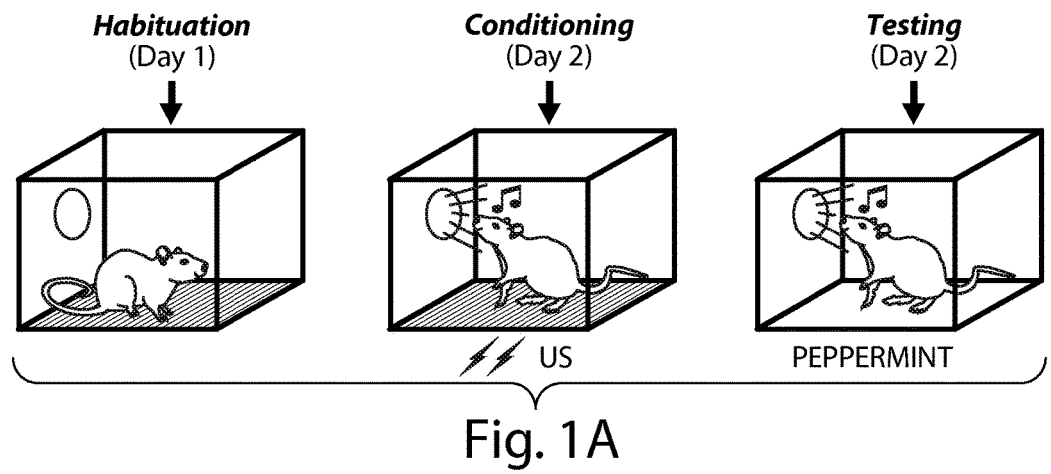
FIGS. 1A-1G. Effect of xenon gas (Xe) on consolidation and reconsolidation of fear memory.
Figure 1B:
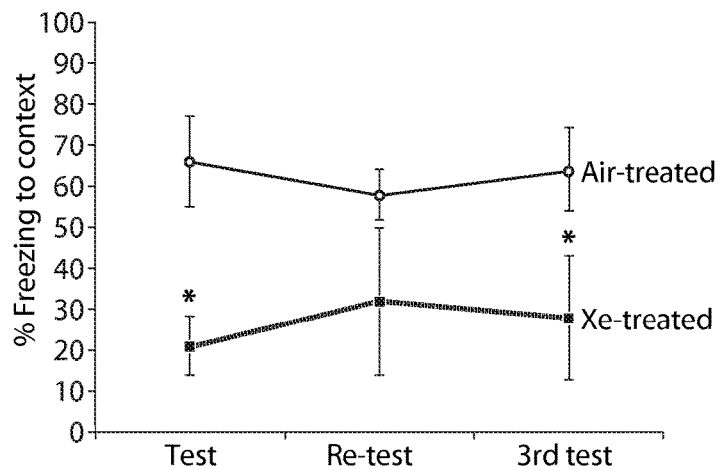
Figure 1C:
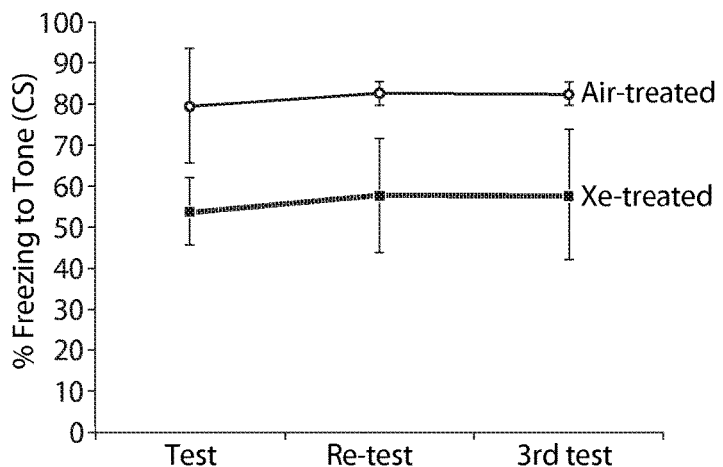

The present invention relates to methods, compositions and kits for the treatment of psychiatric disorders by administration of xenon and/or argon gas in combination with psychotherapy. In some embodiments, the psychotherapy encompasses a variety of, or a combination of any of psychotherapy, cognitive behavioral therapy, psychodynamically oriented treatments. In some embodiments, the psychiatric disorder is any psychological and psychiatric disorders, including but not limited to post-traumatic stress disorder (PTSD), acute stress disorder (ASD), panic disorder, obsessive compulsive disorder (OCD), generalized anxiety disorder (GAD), social anxiety disorder, and phobias. Also contemplated herein are treatments for analogues of these disorders in companion animals (e.g., dogs, cats, pigs, hamsters, guinea pigs, rabbits, etc).

In some embodiments, xenon and/or argon gas or an analogue thereof, is administered to a subject during, prior to, or after the psychotherapy session where the recall of an aversive memory is reactivated by the patient through mental imagery, verbal recall, script recitation, virtual reality (VR) exposure therapy, or other desensitization or flooding exposure therapy. This reactivation of consolidated memories—that are central to sustaining the symptoms of the psychiatric illness—returns the memory to a labile state that is sensitive to disruption by xenon gas given the unique properties of xenon in the brain.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

As used herein, "psychiatric disorder" refers to a disorder that can be treated with the methods of the invention. For purposes of the present invention, an individual said to have a psychiatric disorder will have one or more disorders that can be treated with the methods of the invention. Thus an individual may have a single disorder, or may have a constellation of disorders that are to be treated by the methods described herein.

The term "post-traumatic stress disorder" or "PTSD" as used herein relates to a condition characterized by the development of characteristic symptoms following exposure to a traumatic stressor such as direct personal experience of an event that involves actual or threatened death or serious injury, or other threat to one's physical integrity; or witnessing an event that involves death, injury, or a threat to the physical integrity of another person; or learning about unexpected or violent death, serious harm, or threat of death or injury experienced by a family member or other close associate. The person's response to the event generally involves intense fear, helplessness, or horror. In children, the response generally involves disorganized or agitated behavior. The characteristic symptoms resulting from the exposure to the extreme trauma include persistent reexperiencing of the traumatic event, persistent avoidance of stimuli associated with the trauma and numbing of general responsiveness, and persistent symptoms of increased arousal. In Posttraumatic Stress Disorder, the stressor is generally of extreme nature (c.f. above). In contrast, in Adjustment Disorder, the stressor can be of any severity. The diagnosis of Adjustment Disorder is appropriate both for situations in which the response to an extreme stressor does not meet the criteria for Posttraumatic Stress Disorder (or another specific mental disorder) and for situations in which the symptom pattern of Posttraumatic Stress Disorder occurs in response to a stressor that is not extreme (e.g., spouse leaving, being fired). Symptoms of avoidance, numbing, and increased arousal that are present before exposure to the stressor do not meet criteria for the diagnosis of Posttraumatic Stress Disorder and require consideration of other diagnoses (e.g., Brief Psychotic Disorder, Conversion Disorder, Major Depressive Disorder), these diagnoses should be given instead of, or in addition to, Posttraumatic Stress Disorder. PTSD, as that term is used herein, also encompasses the 4 categories of symptoms outlined in the Diagnostic and Statistical Manual of Mental Disorders 5$^{th}$ Edition (DSM-V) published by the American Psychiatric Association (APA; Washington, D.C., 2013), which include intrusion (e.g., re-experiencing), avoidance, negative alterations in mood and cognition and alterations in arousal and reactivity. Acute Stress Disorder is distinguished from Posttraumatic Stress Disorder because the symptom pattern in Acute Stress Disorder must occur within 4 weeks of the traumatic event and resolve within that 4-week period. If the symptoms persist for more than 1 month and meet criteria for Posttraumatic Stress Disorder, the diagnosis is changed from Acute Stress Disorder to Posttraumatic Stress Disorder. For example, severity of PTSD symptoms can be evaluated by using the Modified PTSD Symptom Scale (PSS) (Coffey et al., J Trauma Stress (1998), 11: 393-399; Falsetti et al., Behav Therapist (1993), 16: 161-162).

As used herein, "anxiety disorder" refers to a disorder characterized by fear, anxiety, addiction, and the like that can be treated with the methods of the invention. An individual who may benefit from the methods of the invention may have a single disorder, or may have a constellation of disorders. The anxiety disorders contemplated in the present invention include, but are not limited to, fear and anxiety disorders, addictive disorders including substance-abuse disorders, and mood disorders. Fear and anxiety disorders include, but are not limited to, panic disorder, specific phobia, post-traumatic stress disorder (PTSD), obsessive-compulsive disorder, and movement disorders such as Tourette's syndrome. The disorders contemplated herein are defined in, for example, the DSM-IV (Diagnostic and Statistical Manual of Mental Disorders (4th ed., American Psychiatric Association, Washington D.C., 1994)).

The term "extinction training" as used herein refers to a method wherein a subject having deleterious, high-anxiety responses to a given stimulus, is exposed to the stimulus such that the conditions of the exposure are manipulated to control the outcome or otherwise reduce the likelihood of an event occurring that would tend to reinforce the fear response. The goal of extinction training is to pair the previously aversive stimulus with a new learning resulting from a non-deleterious outcome resulting from the stimulus, thereby generating in future exposures to the stimulus a more appropriate response in place of the previous deleterious, high-anxiety response. For example, the conditions of the exposure can be manipulated by psychotherapy or pharmacotherapy. In one example of extinction training, a subject having a phobic disorder undergoes extinction training by participating in a traditional exposure-based psychotherapy session. As another example, a subject having erectile dysfunction undergoes extinction training by taking a drug that treats the symptoms of erectile dysfunction (e.g., sildenafil) prior to engaging in a sexual interlude.

The term "reconsolidation" as used herein refers to remembering the memory. Memory consolidation is a category of processes that stabilize a memory trace after the initial acquisition. Consolidation is distinguished into two specific processes, (i) synaptic consolidation, which occurs within the first few hours after learning, and (ii) systems consolidation, where hippocampus-dependent memories become independent of the hippocampus over a period of weeks to years. Reconsolidation is where previously consolidated memories can be made labile again through reactivation of the memory trace. A compound which blocks or inhibits reconsolidation therefore is a compound which prevents the re-integration of the previously consolidated memories, e.g., prevents the subject from remembering the memories.

The term "psychotherapy" refers to a treatment of mental illness, anxiety disorders or emotional disturbances primarily by verbal or non-verbal communication.

The term "xenon composition" means any gas that includes xenon, any liquid in which xenon gas is dissolved or suspended, and any solid in which xenon gas is entrapped or encapsulated (e.g., nanoparticles or nanosponges). Similarly, the term "argon composition" means any gas that includes argon, any liquid in which argon gas is dissolved or suspended, and any solid in which xenon gas is entrapped or encapsulated (e.g., nanoparticles or nanosponges).

As used herein, a "high-anxiety response" refers to a subject's response to a given stimulus, wherein the response is characterized by a high level of anxiety that is disproportionate to the threat represented by the stimulus. Accordingly, a stimulus that generates little if any anxiety in most subjects would generate substantial anxiety in a subject undergoing a deleterious, high-anxiety response. These deleterious, high-anxiety responses cause or exacerbate symptoms characteristic of the medical disorders described herein.

As used herein, a pharmacologic agent that "hastens the rate of extinction" refers to a compound that, when administered to rats according to the experimental procedures described herein, significantly reduces the extent of fear expression in treated rats (relative to untreated animals) in response to a conditioned stimulus.

The terms "lower", "reduced", "reduction" or "decrease" or "inhibit" are all used herein generally to mean a decrease by a statistically significant amount. However, for avoidance of doubt, "lower", "reduced", "reduction" or "decrease" or "inhibit" means a measurable, observable, or detectable decrease, such as a decrease by at least 5%, 10%, 15%, 20%, 25%, 30%, 35%, 40%, 45%, 50%, 55%, 60%, 65%, 70%, 75%, 80%, 85%, 90%, or 95%. In some embodiments, a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The term "inhibiting" as used herein as it pertains to the expression or activity of a protein or polypeptide does not necessarily mean complete inhibition of expression and/or activity. Rather, expression or activity of the protein, polypeptide or polynucleotide is inhibited to an extent, and/or for a time, sufficient to produce the desired effect.

The terms "increased", "increase" or "enhance" or "higher" are all used herein to generally mean an increase by a statically significant amount; for the avoidance of any doubt, the terms "increased", "increase" or "enhance" or "higher" means a measurable, observable, or detectable increase, such as an increase of at least 5%, 10%, 15%, 20%, 25%, 30%, 35%, 40%, 45%, 50%, 55%, 60%, 65%, 70%, 75%, 80%, 85%, 90%, 95%, or 100%, or any increase between 10-100%, or at least about a 2-fold, or at least about a 3-fold, or at least about a 4-fold, or at least about a 5-fold or at least about a 10-fold increase, or any increase between 2-fold and 10-fold or greater as compared to a reference level.

The term "drug", "agent" or "compound" as used herein refers to a chemical entity or biological product, or combination of chemical entities or biological products, administered to a person to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The term "agent" refers to any entity which is normally absent or not present at the levels being administered, in the cell. Agent may be selected from a group comprising; chemicals; small molecules; nucleic acid sequences; nucleic acid analogues; proteins; peptides; aptamers; antibodies; or fragments thereof. A nucleic acid sequence may be RNA or DNA, and may be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. The agent may be applied to the media, where it contacts the cell and induces its effects. Alternatively, the agent may be intracellular within the cell as a result of introduction of the nucleic acid sequence into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The term "antagonist" refers to any agent or entity capable of inhibiting the expression or activity of a protein, polypeptide portion thereof, or polynucleotide. In some embodiments, the term "antagonist" refers to a compound or agent which blocks a receptor from activation by agonists. Thus, the antagonist may operate to prevent transcription, translation, post-transcriptional or post-translational processing or otherwise inhibit the activity of the protein, polypeptide or polynucleotide in any way, via either direct or indirect action. The antagonist may for example be a nucleic acid, peptide, or any other suitable chemical compound or molecule or any combination of these. Additionally, it will be understood that in indirectly impairing the activity of a protein, polypeptide of polynucleotide, the antagonist may affect the activity of the cellular molecules which may in turn act as regulators or the protein, polypeptide or polynucleotide itself. Similarly, the antagonist may affect the activity of molecules which are themselves subject to the regulation or modulation by the protein, polypeptide of polynucleotide. In some embodiments, the term "antagonist" as used in reference to an antagonist of NMDA receptor includes any compound that reduces the flow of cations through an ionotropic receptor such as the NMDA receptor, i.e., a channel closer, and which has not been observed to increase the flow of cations through the same receptor.

The term "agonist" refers as used herein refers to an agent capable of increasing the activity of a protein, polypeptide or polynucleotide or receptor. In some embodiments, the term "agonist" as used herein in reference to an agonist of the NMDA receptor refers to any compound that increases the flow of cations through an ionotrophic receptor such as the NMDA receptor, i.e., a channel opener, and which has not been observed to decrease the flow of cations through the same receptor.

The terms "partial agonist" or "partial antagonist" as used herein refers to a compound that regulates an allosteric site on an ionotropic receptor. In some embodiments, a partial agonist as used in reference to a partial agonist of the NMDA receptor refers to a compound which increases or decrease the flux of cations through the ligand-gated channel depending on the presence or absence of the principal site ligand, that is, in the presence or absence of a known endogenous ligand binding to a site on the receptor. In the absence of the principal site ligand, a partial agonist increases the flow of cations through the ligand-gated channel, but at a lower flux than achieved by the principal site ligand. A partial agonist partially opens the receptor channel. In the presence of the principal site ligand, a partial agonist decreases the flow of cations through the ligand-gated channel below the flux normally achieved by the principal site ligand. Xenon as used herein is a blocker of the glycine site (glycine is a co-agonist of the NMDA receptor) on the NMDA receptor. Thus, xenon competes with glycine and functions as a partial antagonist, preventing a conformational change in the NMDA receptor which, in the presence of glutamate (the primary ligand for the NMDA receptor), reduces the cation and calcium flow through the receptor.

The term "co-agonist" as used herein refers to a compound which functions in conjunction with a second compound to activate a receptor. Typically, a co-agonist works with other co-agonists to produce the desired effect together. For example, the NMDA receptor activation requires the binding of both of its glutamate and glycine co-agonists.

The term "competitive antagonist" as used herein refers to an antagonist, e.g., an inhibitor which binds to the active site of the molecule which it is inhibiting preventing the normal receptor ligand (e.g., agonist) from binding to the active site. Most competitive inhibitors (e.g., competitive antagonists) function by binding reversibly to the active site of the enzyme. For example, allosteric inhibitors may display competitive, non-competitive, or uncompetitive inhibition.

As used herein, the term "NMDA receptor" or "NMDA channel" refers to the glutamate receptor channel NMDA subtype (Yamakura and Shimoji (1999) Prog. Neurobiol. 59(3):279-298).

As used herein, "NMDA receptor agonist," "NMDA receptor antagonist," and "NMDA receptor partial agonist," may be alternately referred to as "NMDA agonist," "NMDA antagonist," and "NMDA partial antagonist," respectively. Also, "NMDA receptor partial agonist" is intended to be interchangeable with "partial NMDA receptor agonist."

The terms "patient", "subject" and "individual" are used interchangeably herein, and refer to an animal, particularly a human, to whom treatment, including prophylactic treatment is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. In another embodiment, the subject is a domesticated animal including companion animals.

The term "chronic administration" means the administration of an agent (e.g., a xenon composition as described herein) on a periodic basis (e.g., at least once a day, twice a day, three times a day, four times a day, at least once a week, twice a week, three times a week, four times a week, five times a week, six times a week, seven times a week, once a month, twice a month, three times a month, and four times a month) over an extended period of time (e.g., at least one month, two months, three months, four months, five months, six months, seven months, eight months, nine months, ten months, eleven months, one year, two years, three years, four years, five years, six years, seven years, eight years, nine years, or ten years). The periodic administration of the agent (e.g., a xenon composition as described herein) can be performed over a continuous period of time (as described herein) or can be administered as a bolus (e.g., inhalation of a single dose of xenon gas or administration of a dosage of a xenon composition (e.g., a nanoparticle or nanosponge).

The phrase "continuous period of time" means at least 5 minutes, (e.g., at least 10 minutes, at least 15 minutes, 30 minutes, 45 minutes, 1 hour, 2 hours, 3 hours, 4 hours, 5 hours, 6 hours, 7 hours, 8 hours, 9 hours, 10 hours, 11 hours, or 12 hours, overnight, or between 5 and 13 hours).

As used herein, "acute" administration of a therapeutic means a single exposure within an extended time period of the subject to the therapeutically effective amount of the pharmacologic agent that facilitates extinction. In conjunction with this definition of "acute", an extended time period is defined as four days or longer, e.g., once-weekly administration of a cannabinoid reuptake inhibitor constitutes acute administration. Administering a dose of a xenon and/or argon composition to a subject, followed by a second dose 24 hours later, does not constitute acute dosing. Administering a single dose of a xenon and/or argon composition, wherein the dose is formulated to have both immediate release and delayed release characteristics, constitutes acute dosing provided that the peak blood level of the a xenon and/or argon composition in the subject is achieved within 12 hours of the time the dose is administered.

As used herein, a subject is "treated", or subjected to "treatment", when an earnest attempt is made to alleviate a medical disorder or disease. For example, a subject can be treated for a disorder by being administered a pharmacologic agent that is intended to alleviate the disorder, irrespective of whether the treatment actually was successful in alleviating the disorder.

As used herein, a disease or disorder or medical affliction is "alleviated" if either (or both) the severity or frequency of a symptom of the disease or disorder or medical affliction is reduced.

A "subject" of diagnosis or treatment is a mammal.

A "therapeutic" treatment is a treatment administered to a subject who exhibits signs of pathology for the purpose of diminishing or eliminating those signs.

A "therapeutically effective amount" or "therapeutically effective dose" of the pharmacologic agent is an amount of the pharmacologic agent that, when administered in conjunction with psychotherapy, e.g., extinction training, results in an improved therapeutic benefit relative to that observed with extinction training in the absence of administering the pharmacologic agent. The exact amount required will vary depending on factors, such as the species being treated, genetic sensitivity, the age and general condition of the subject, the severity of the psychiatric disorder, the mode of administration and so forth. Thus, it is not possible to specify the exact "effective amount". However, for any given case, an appropriate "effective amount" may be determined by one of ordinary skill in the art using only routine experimentation. For example, an effective amount using the methods as disclosed herein would be considered as the amount sufficient to reduce the onset of the anxiety-triggering event, e.g., a symptom of the anxiety. Further, an effective amount as used herein would also include an amount of xenon composition to delay the onset of one or more symptoms of a psychiatric disorder or eliminate a symptom of the psychiatric disease or disorder.

The term "treating" or "treatment" as used herein, means administering a xenon composition in an amount effective to cause a reduction in the severity, duration, or frequency of one or more symptoms of a psychiatric disorder, or delay the onset of one or more symptoms of a psychiatric disorder in a subject. A delay in the onset of one or more symptoms of a psychiatric disorder in a subject chronically administered a xenon composition can be compared to the development of the same symptoms in a subject with the same disease (e.g., same psychiatric disorder) not administered the xenon composition, or a subject having the same disease that is not chronically administered the xenon composition.

The term "delaying the onset" means decreasing the rate of development or delaying the development of one or more symptoms of a psychiatric disorder as disclosed herein in a subject by administering a therapeutic treatment (e.g., administration of a xenon composition) compared to a control subject (e.g., a subject not receiving the therapeutic treatment or rate of the development of symptoms in the same subject prior to therapeutic treatment).

The phrase "symptom of a psychiatric disorder" means a physical, behavioral, or cognitive manifestation of a psychiatric disorder that can be assessed or measured by a health care professional (e.g., a physician, a nurse, a physician's assistant, or a laboratory technician). Non-limiting examples of symptoms of a psychiatric disorder, such as an anxiety disorder include: sudden attacks of intense fear or anxiety, usually associated with numerous physical symptoms such as heart palpitations, rapid breathing or shortness of breath, blurred vision, dizziness, and racing thoughts; tremor, slowed motion, rigid muscles, impaired posture, impaired balance, loss of automatic movements, speech impairment, personality changes, decreased cognitive abilities, clumsiness, involuntary facial movements, jerky or rapid eye movements, seizures, swallowing problems, weakness or numbness in arms, legs, feet, or ankles, muscle cramps, disorientation, difficulty breathing, high heart rate, changes in blood pressure, changes in galvanic skin conductance (GSR), difficulty concentrating, partial or complete loss of vision, double or blurred vision, dizziness, temporary confusion, uncontrollable jerking movements, loss of consciousness, impairment in ability to learn or remember new information, impairment in ability to reason, paranoia, agitation, and hallucinations. Psychiatric Diagnoses are categorized by the Diagnostic and Statistical Manual of Mental Disorders, 4th. Edition, (also known as the DSM-IV) or the Diagnostic and Statistical Manual of Mental Disorders $5^{th}$ Edition (also known as the DSM-V) published by the American Psychiatric Association and covers all mental health disorders for both children and adults. It also lists known causes of these disorders, statistics in terms of gender, age at onset, and prognosis as well as some treatment approaches The phrase "a subject at risk for developing a psychiatric disorder" means a subject who has been identified as having an increased likelihood of developing a psychiatric disorder compared to a control population (e.g., the general population or a sex-matched and/or age-matched population). The assessment of risk in a subject can be determined by a number of factors known in the art, including, but not limited to, family history of disease, genetic testing for one or more genes associated with a psychiatric disorder, estrogen levels, exposure to environmental toxins (e.g., lead exposure), low levels of B vitamin folate, head trauma, cardiovascular disease, type 2 diabetes, oxidative damage, inflammation, and smoking. In some embodiments, a subject at risk of developing a psychiatric disorder is a subject at risk of developing PTSD, and can be identified according to the methods as disclosed in US Patent Application 2011/0295166, which is incorporated herein in its entirety by reference.

A "nanoparticle" or "nanosponge" is a solid particle that contains a crosslinked solid skeleton (e.g., cyclodextrin) and a core containing a gas, which spontaneously releases the gas (e.g., xenon gas) or that can be disrupted (e.g., disrupted in the tissue of a subject) upon exposure to ultrasonic waves. Non-limiting examples of nanosponges have a diameter of less than 550 nm Methods for the preparation of these nanosponges are known in the art (see, e.g., Cavalli et al., Int. J. Pharm. 404:254-257, 2010). A non-limiting example of a nanoparticle is a liposome (e.g., an echogenic liposome).

An "echogenic liposome" is a vesicle that contains a phospholipid bilayer and a core (e.g., a core containing xenon gas), that can be disrupted (e.g., disrupted in the tissue of a subject) upon exposure to ultrasonic waves. Non-limiting examples of echogenic liposomes have a diameter of less than 5 µm, 4 µm, 3 µm, 2 µm, or 1 µm. Methods for the preparation of these liposomes are known in the art (see, e.g., Britton et al., Circulation 122:1578-1587, 2010).

The term "percent saturated" means the amount of gas (e.g., xenon and/or argon gas) dissolved in a fluid at a specific temperature and pressure compared to the maximum amount of gas (e.g., xenon and/or argon gas) that can be dissolved in the same fluid at the same temperature and pressure.

As used herein, "biofeedback" refers to a technique in which subjects are trained to improve their health by using signals from their own bodies to control their own physiological responses. Biofeedback is particularly useful in enabling subjects to learn to control physiological processes that normally occur involuntarily, such as blood pressure, heart rate, muscle tension, and skin temperature.

Compositions or methods "comprising" one or more recited elements may include other elements not specifically recited. For example, a composition that comprises a fibril component peptide encompasses both the isolated peptide and the peptide as a component of a larger polypeptide sequence. By way of further example, a composition that comprises elements A and B also encompasses a composition consisting of A, B and C. The terms "comprising" means "including principally, but not necessary solely". Furthermore, variation of the word "comprising", such as "comprise" and "comprises", have correspondingly varied meanings. The term "consisting essentially" means "including principally, but not necessary solely at least one", and as such, is intended to mean a "selection of one or more, and in any combination." In the context of the specification, the term "comprising" means "including principally, but not necessary solely". Furthermore, variation of the word "comprising", such as "comprise" and "comprises", have correspondingly varied meanings.

The use of the word "a" or "an" when used in conjunction with the term "comprising" in the claims and/or the specification may mean "one" but is also consistent with the meaning of "one or more", "at least one" and "one or more than one."

Other than in the operating examples, or where otherwise indicated, all numbers expressing quantities of ingredients or reaction conditions used herein should be understood as modified in all instances by the term "about." The term "about" when used in connection with percentages can mean±1%.

This invention is further illustrated by the following examples which should not be construed as limiting. The contents of all references cited throughout this application, as well as the figures and tables are incorporated herein by reference.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Psychiatric Disorders

In some embodiments, a xenon and/or argon composition is administered (or self-administered) to a subject who is in need of treatment, e.g., a subject who has at least one symptom of a psychiatric disorder as disclosed herein. Psychiatric disorders contemplated in the present invention include, but are not limited to, fear and anxiety disorders, addictive disorders including substance-abuse disorders, and mood disorders. Within the fear and anxiety disorder category, the invention encompasses the treatment of panic disorder, specific phobia, post-traumatic stress disorder (PTSD), obsessive-compulsive disorder, and movement disorders. The disorders contemplated herein are defined in, for example, the DSM-IV (Diagnostic and Statistical Manual of Mental Disorders (4th ed., American Psychiatric Association, Washington D.C., 1994)), or the DSM-V (Diagnostic and Statistical Manual of Mental Disorders (5$^{th}$ Edition, American Psychiatric Association, Washington, D.C., 2013), which are herein incorporated by reference in their entirety. In some embodiments, a subject amenable to treatment is a subject with at least one symptom of PTSD as disclosed herein.

Anxiety Disorders

The methods of the invention contemplate treatment of anxiety disorders by combining (i) administration of a xenon and/or argon composition to a subject; and (ii) desensitization training provided by any type of psychotherapy that is suitable for the particular anxiety disorder for which the subject is undergoing treatment. Suitable methods of psychotherapy include, but are not limited to, exposure-based psychotherapy, cognitive psychotherapy, and psychodynamically oriented psychotherapy.

In some embodiments, the methods and compositions as disclosed herein can be used to treat a psychiatric disorder which is a fear and/or anxiety related disorder. Such anxiety related disorders include, but are not limited to Acute Stress Disorder, Agoraphobia (with or without a history of Panic Disorder), Generalized Anxiety Disorder (GAD), Obsessive-Compulsive Disorder (OCD), Panic Disorder (with or without Agoraphobia), Phobias (including Social Phobia), and Posttraumatic Stress Disorder (PTSD). In some embodiments, the methods and compositions as disclosed herein can be used to treat a psychiatric disorder which is a fear and/or anxiety related disorder, including but not limited to, acute stress disorder (ASD), panic disorder, generalized anxiety disorder (GAD), social anxiety disorder, phobias, and addiction disorders.

Acute Stress Disorder:

Acute stress disorder is a result of a traumatic event in which the person experienced or witnessed an event that involved threatened or actual serious injury or death and responded with intense fear and helplessness. Symptoms include dissociative symptoms such as numbing, detachment, a reduction in awareness of the surroundings, derealization, or depersonalization; re-experiencing of the trauma, avoidance of associated stimuli, and significant anxiety, including irritability, poor concentration, difficulty sleeping, and restlessness. The symptoms must be present for a minimum of two days and a maximum of four weeks and must occur within four weeks of the traumatic event for a diagnosis to be made.

Agoraphobia:

Agoraphobia can develop out of simple phobias or it can be a result of extreme trauma, although it is often a result of numerous panic attacks such as those found in panic disorder. Agoraphobia, like other phobias, is made up of extreme anxiety and fear. Different from other phobias, however, is the generalization which occurs. Agoraphobia is the anxiety about being in places where escape might be difficult or embarrassing or in which help may not be available should a panic attack develop. It can be sub diagnosed as either 'with' or 'without' panic disorder (see above). Typically situations that invoke anxiety are avoided and in extreme cases, the person may never or rarely leave their home.

General Anxiety Disorder (GAD):

Often anxiety gets generalized to other situations, and can then become overwhelming or associated with life in general. Typically GAD develops over a period of time and may not be noticed until it is significant enough to cause problems with functioning. GAD is evidenced by general feelings of anxiety such as mild heart palpitations, dizziness, and excessive worry. The symptoms are difficult to control for the individual and are not related to a specific event (such as in PTSD) and are not as severe as those found with Panic Disorder.

Obsessive Compulsive Disorder (OCD):

The key features of OCD include obsessions (persistent, often irrational, and seemingly uncontrollable thoughts) and compulsions (actions which are used to neutralize the obsessions). A good example of this would be an individual who has thoughts that he is dirty, infected, or otherwise unclean which are persistent and uncontrollable. In order to feel better, he washes his hands numerous times throughout the day, gaining temporary relief from the thoughts each time. For these behaviors to constitute OCD, it must be disruptive to everyday functioning (such as compulsive checking before leaving the house making you extremely late for all or most appointments, washing to the point of excessive irritation of your skin, or inability to perform everyday functions like work or school because of the obsessions or compulsions).

Panic Disorder (with or without Agoraphobia).

Often the symptoms of a panic disorder come on rapidly and without an identifiable stressor. The individual may have had periods of high anxiety in the past, or may have been involved in a recent stressful situation. The underlying causes, however, are typically subtle. Panic Disorder is characterized by sudden attacks of intense fear or anxiety, usually associated with numerous physical symptoms such as heart palpitations, rapid breathing or shortness of breath, blurred vision, dizziness, and racing thoughts. Often these symptoms are thought to be a heart attack by the individual, and many cases are diagnosed in hospital emergency rooms.

Simple Phobias (Including Social Phobia):

Often a traumatic event is the precursor for a phobia, which may or may not be at the conscious level. Symptoms of a phobia include either extreme anxiety and fear associated with the object or situation or avoidance. To be diagnosed, the symptoms must be disruptive to everyday functioning (such as quitting a great job merely because you have to use an elevator). Phobias encompassed for treatment herein include vertigo, fear of flying, as well as specific phobias such as a fear of a single specific panic trigger, and include, for example, spiders, snakes, dogs, water, heights, flying, catching a specific illness, fear of the dark, fear of sexual abuse, etc.

Post-Traumatic Stress Disorder (PTSD):

By definition, a diagnosis of PTSD requires exposure to a traumatic event which causes intense fear and/or helplessness in an individual. PTSD can occur after the subject has seen, experienced or learned about a traumatic event that involved the threat of injury or death either to themselves or a loved one. Typically the symptoms develop shortly after the event, but may take years. The duration for symptoms is at least one month for this diagnosis. Symptoms of PTSD include re-experiencing the trauma through traumatic memories, nightmares, obsessive thoughts, and flashbacks (feeling as if you are actually in the traumatic situation again). There is an avoidance component as well, where the individual avoids situations, people, and/or objects which remind him or her about the traumatic event (i.e. a person experiencing PTSD after a serious car accident might avoid driving or being a passenger in a car). Another cluster of symptoms include negative alterations in cognition and mood associated with the traumatic event. These symptoms include persistent and exaggerated negative beliefs about oneself or the world, persistent negative emotional states (e.g. fear, horror, anger guilt, shame), markedly diminished interest in significant activities (i.e. inability to find pleasurable things rewarding), feelings of detachment and emotional numbing. Finally, there is increased arousal in general, including an exaggerate startle response (hyperarousal), irritability and aggression, reckless or destructive behavior, problems with concentration, and sleep disturbances. A subject suffering from PTSD can be any age, gender and socioeconomic status, and can be the result of the subject experiencing a natural disaster such as an excessive storm, flood or fire, earthquake, or an event such as, but not limited to, assault (including sexual assault), battery, domestic abuse, prison stay, rape, terrorism, war, violent accident, work-related or vehicular accident (e.g., car or airplane accident), explosion etc. For example, the terrorist attacks of Sep. 11, 2001 may have caused PTSD in some people who were involved, in people who saw the disaster, and in people who lost relatives and friends. Veterans returning home from a war often have PTSD. The cause of PTSD is unknown. Psychological, genetic, physical, and social factors are involved. PTSD changes the body's response to stress. It affects the stress hormones and chemicals that carry information between the nerves (neurotransmitters). A subject having a history of early-life stress may increase the risk of that subject developing PTSD after a recent traumatic event.

Symptoms of PTSD fall into several main categories: reliving the event (e.g., reliving the event through intrusive thought), avoidance (including mood and cognitive disruptions), and arousal.

1. "Reliving" the event, which disturbs day-to-day activity includes symptoms such as: flashback episodes, where the event seems to be happening again and again; repeated upsetting memories of the event; repeated nightmares of the event, strong, uncomfortable reactions to situations that remind the subject of the event.

2. Avoidance symptoms of PTSD include symptoms such as, for example: emotional "numbing," or feeling as though the subject doesn't care about anything; feeling detached; being unable to remember important aspects of the trauma; having a lack of interest in normal activities; decreased showing of the subjects moods; avoiding places, people, or thoughts that remind the subject of the event; a feeling that the subject has no future.

3. Arousal symptoms of PTSD include symptoms such as; difficulty concentrating; startling easily; having an exaggerated response to things that startle the subject; feeling more aware (hyper vigilance); feeling irritable or having outbursts of anger; having trouble falling or staying asleep; feelings of guilt about the event (including "survivor guilt"). Other symptoms of PTSD include symptoms typical of anxiety, stress, and tension such as: agitation or excitability, dizziness, fainting, a feeling of the subjects heart beat in their chest (heart palpitations), headache.

There are five main types of post-traumatic stress disorder encompassed for treatment with the methods as disclosed herein and include, normal stress response, acute stress disorder, uncomplicated PTSD, comorbid PTSD and complex PTSD. Normal Stress Response occurs when healthy adults who have been exposed to a single discrete traumatic event in adulthood experience intense bad memories, emotional numbing, feelings of unreality, being cut off from relationships or bodily tension and distress.

Acute Stress disorder is characterized by panic reactions, mental confusion, dissociation, severe insomnia, suspiciousness, and being unable to manage even basic self-care, work, and relationship activities. Survivors of single traumas can sometimes have this more severe reaction, especially when the trauma is a lasting catastrophe that exposes them to death, destruction, or loss of home and community Uncomplicated PTSD involves persistent and often spontaneously re-experiencing of the traumatic event, avoidance of stimuli associated with the trauma, emotional numbing, and symptoms of increased arousal. Comorbid PTSD is actually much more common than uncomplicated PTSD. PTSD is usually associated with at least one other major psychiatric disorder such as depression, alcohol or substance abuse, panic disorder, and other anxiety disorders. Complex PTSD (sometimes called "Disorder of Extreme Stress") is found among individuals who have been exposed to prolonged traumatic circumstances, especially during childhood, such as childhood sexual abuse. These individuals often are diagnosed with borderline or antisocial personality disorder or dissociative disorders. They exhibit behavioral difficulties (such as impulsivity, aggression, sexual acting out, eating disorders, alcohol or drug abuse, and self-destructive actions), extreme emotional difficulties (such as intense rage, depression, or panic) and mental difficulties (such as fragmented thoughts, dissociation, and amnesia).

In some embodiments, the methods and xenon and/or argon compositions as disclosed herein can be used to treat a psychiatric disorder which is selected from the group consisting of: Adjustment Disorders, anxiety Disorders, dissociative Disorders, eating Disorders, Impulse-Control Disorders, Mood Disorders, Sexual Disorders, Sleep Disorders, Psychotic Disorders, Sexual Dysfunctions, Somatoform Disorders, Substance Disorders, Personality Disorders. Identification of subjects with these disorders are well known to a person of ordinary skill in the art, and are categorized by the Diagnostic and Statistical Manual of Mental Disorders, 4th. Edition, which is incorporated herein in its entirety by reference.

Addiction:

In some embodiments, the psychiatric disorder is addiction, e.g., but not limited to, a drug and/or alcohol dependency, an eating disorder (e.g., anorexia or bulimia) etc. In some embodiments, the xenon and/or argon composition is administered to a subject during and/or after a psychotherapy session during a drug craving, or during withdrawal anhedonia. Withdrawal anhedonia is an aversive state that is central to sustaining drug abuse and dependence. In some embodiments, a xenon and/or argon composition is administered to a subject during and/or after a psychotherapy session for the treatment of an addiction. Addiction is the continued use of a mood altering substance or behavior despite adverse consequences, or a neurological impairment leading to such behaviors.

Addictions can include, but are not limited to, drug (including alcohol) abuse, exercise addiction, sexual addiction, food addiction, lack of food addiction (anorexia), and gambling. Classic hallmarks of addiction include impaired control over substances or behavior, preoccupation with substance or behavior, continued use despite consequences, and denial. Habits and patterns associated with addiction are typically characterized by immediate gratification (short-term reward), coupled with delayed deleterious effects (long-term costs).

Addiction as used herein also encompasses compulsions that are not substance-related, such as compulsive shopping, sex addiction/compulsive sex, eating disorders, overeating, under-eating (e.g., Anorexia nervosa), problem gambling, exercise/sport and computer addiction. Sometimes the compulsion is not to "do" something but to avoid or "do nothing" e.g. procrastination (compulsive task avoidance). In these kinds of common usages, the term addiction is used to describe a recurring compulsion by an individual to engage in some specific activity, despite harmful consequences, as deemed by the user themselves to their individual health, mental state, or social life.

Physiological dependence occurs when the body has to adjust to the substance by incorporating the substance into its 'normal' functioning. This state creates the conditions of tolerance and withdrawal. Tolerance is the process by which the body continually adapts to the substance and requires increasingly larger amounts to achieve the original effects. Withdrawal refers to physical and psychological symptoms experienced when reducing or discontinuing a substance that the body has become dependent on. Symptoms of withdrawal generally include but are not limited to anxiety, irritability, intense cravings for the substance, nausea, hallucinations, headaches, cold sweats, and tremors.

Psychotherapy

The methods of the invention encompass the use of any type of psychotherapy that is suitable for the particular psychiatric disorder for which the individual is undergoing treatment. Suitable methods of psychotherapy include, but are not limited to, exposure-based psychotherapy, cognitive psychotherapy, and psychodynamically oriented psychotherapy. See, for example, Foa (2000) J. Clin. Psych. 61(suppl. 5):43-38.

One method of psychotherapy contemplated is the use of virtual reality (VR) exposure therapy to treat a psychiatric disorder using the combination therapy protocol of the invention. VR exposure therapy has been used to treat a variety of disorders including anxiety disorders such as the fear of heights (Rothbaum and Hodges (1999) Behav. Modif. 23(4):507-25), as well as specific phobias, eating disorders, and PTSD (Anderson et al. (2001) Bull. Menninger Clin. 65(1):78-91). Because of the prevalence of PTSD in the general population and the successful use of VR therapy to treat PTSD in, for example, Vietnam veterans (Rothbaum et al. (1999) J. Trauma Stress 12(2):263-71) or rape victims (Rothbaum et al. (2001) J. Trauma Stress 14(2):283-93), one embodiment of the present invention specifically contemplates the use of such VR exposure psychotherapy in combination with a pharmacologic agent as described elsewhere herein to treat PTSD.

Psychotherapy useful in the methods as disclosed herein includes the therapeutic interaction or treatment contracted between a trained professional and a client, patient, family, couple, or group. Psychotherapy aims to increase the individual's sense of his/her own well-being. Psychotherapists employ a range of techniques based on experiential relationship building, dialogue, communication and behavior change that are designed to improve the mental health of a client or patient, or to improve group relationships (such as in a family). Psychotherapy may also be performed by practitioners with a number of different qualifications, including psychiatry, clinical psychology, counseling psychology, clinical or psychiatric social work, mental health counseling, marriage and family therapy, rehabilitation counseling, school counseling, play therapy, music therapy, art therapy, drama therapy, dance/movement therapy, occupational therapy, psychiatric nursing, psychoanalysis and those from other psychotherapies.

Psychotherapy often includes techniques to increase awareness and the capacity for self-observation, change behavior and cognition, and develop insight and empathy. A desired result enable other choices of thought, feeling or action; to increase the sense of well-being and to better manage subjective discomfort or distress. Perception of reality is hopefully improved. Grieving might be enhanced producing less long term depression. Psychotherapy can improve medication response where such medication is also needed. Psychotherapy can be provided on a one-to-one basis, in group therapy, conjointly with couples and with entire families. It can occur face to face (individual), over the telephone, or, much less commonly, the Internet. Its time frame may be a matter of weeks or many years. Therapy may address specific forms of diagnosable mental illness, or everyday problems in managing or maintaining interpersonal relationships or meeting personal goals. Treatment in families with children can favorably influence a child's development, lasting for life and into future generations. Better parenting may be an indirect result of therapy or purposefully learned as parenting techniques. Divorces can be prevented, or made far less traumatic. Treatment of everyday problems is more often referred to as counseling (a distinction originally adopted by Carl Rogers) but the term is sometimes used interchangeably with "psychotherapy". Therapeutic skills can be used in mental health consultation to business and public agencies to improve efficiency and assist with coworkers or clients.

In some embodiments, a psychotherapy session useful in the methods as disclosed herein can include one or more approaches; Psychoanalysis, Gestalt therapy, Positive Psychotherapy, Group psychotherapy, Cognitive behavioral therapy, Behavior therapy, Body-oriented psychotherapy, Expressive therapy, Interpersonal psychotherapy, Narrative therapy, Integrative psychotherapy, Hypnotherapy, Meta-psychiatry, Adaptations for children.

In some embodiments, a psychotherapy session encompassed in the methods as disclosed herein can be cognitive behavioral therapy or behavior therapy. Cognitive behavioral therapy (CBT) refers to a range of techniques which focus on the construction and re-construction of people's cognitions, emotions and behaviors. Generally in CBT, the therapist, through a wide array of modalities, helps clients assess, recognize and deal with problematic and dysfunctional ways of thinking, emoting and behaving.

Behavior therapy focuses on modifying overt behavior and helping clients to achieve goals. This approach is built on the principles of learning theory including operant and respondent conditioning, which makes up the area of applied behavior analysis or behavior modification. This approach includes acceptance and commitment therapy, functional analytic psychotherapy, and dialectical behavior therapy. Sometimes it is integrated with cognitive therapy to make cognitive behavior therapy. By nature, behavioral therapies are empirical (data-driven), contextual (focused on the environment and context), functional (interested in the effect or consequence a behavior ultimately has), probabilistic (viewing behavior as statistically predictable), monistic (rejecting mind-body dualism and treating the person as a unit), and relational (analyzing bidirectional interactions).

In some embodiments, a psychotherapy session encompassed in the methods as disclosed herein can be selected from or any combination of group psychotherapy, Cognitive-Behavioral Therapy, Eye movement desensitization and reprocessing (EMDR), Emotional Freedom Technique (often referred to as "tapping"), hypnosis or hypnotherapy.

Group psychotherapy is a beneficial psychotherapy method for PTSD, especially for military personnel and veterans. Group treatment is practiced in VA PTSD Clinics and Vet Centers for military veterans and in mental health and crisis clinics for victims of assault and abuse. A group of peers enables subjects to share traumatic material with the safety, cohesion, and empathy provided by other survivors. As they work through trauma-related shame, they may experience feelings of guilt, rage, fear, doubt, and self-condemnation. Telling one's story (the "trauma narrative") enables the subject to directly face the grief, anxiety, and guilt related to trauma.

Cognitive-Behavioral Therapy (CBT) is a relatively structured kind of psychotherapy involving teaching the patient specific techniques within a limited number of sessions. The subject can practice with "homework exercises" between sessions, and optionally can be administered a xenon and/or argon composition during or after such sessions. Specific techniques in therapy for PTSD include exposure and cognitive restructuring. Other techniques, such as relaxation, self-talk and assertiveness training may also be used. Exposure therapy involves gradually facing the thoughts and memories of the traumatic event or situations (places where the event occurred) that make one anxious. This can be done by using imaging techniques or by actually returning to the place where one had an accident.

Exposure therapy is intended to help the patient face and gain control of the fear and distress that was overwhelming in the trauma, and must be done very carefully in order not to re-traumatize the patient. In some cases, trauma memories or reminders can be confronted all at once ("flooding"), while for other individuals or traumas it is preferable to work gradually up to the most severe trauma by using relaxation techniques and either starting with less upsetting life stressors or by taking the trauma one piece at a time ("desensitization"). Cognitive restructuring involves identifying irrational (but understandable) patterns of thought, feeling and behavior that emerge after a traumatic event. The person gradually learns to substitute new thoughts (for example, a raped women who sees all men as untrustworthy may revise perceptions of some men), and so to develop new emotional and behavioral patterns (for example, learning to date again or discovering how to enjoy sex again). Additional cognitive-behavioral techniques may involve learning skills for coping with anxiety (such as breathing retraining or biofeedback) and negative thoughts ("cognitive restructuring"), managing anger, preparing for stress reactions ("stress inoculation"), handling future trauma symptoms and urges to use alcohol or drugs when they occur ("relapse prevention"), and communicating and relating effectively with people ("social skills" or marital therapy).

Eye movement desensitization and reprocessing (EMDR) is also encompassed for use in the methods as disclosed herein, in which the subject looks at the memories of the trauma (including all of the negative thoughts, feelings and sensations experienced at the time of the event). EMDR aims to change how the subject feels about these memories and helps the subject to have more positive emotions, behavior and thoughts. During EMDR, the subject will be asked to concentrate on an image connected to the traumatic event and the related negative emotions, sensations and thoughts, while paying attention to something else, usually the therapist's fingers moving from side to side in front of your eyes. After each set of eye movements (about 20 seconds), the subject is encouraged to let go of the memories and discuss the images and emotions experienced during the eye movements. This process is repeated, this time with a focus on any difficult, persisting memories. Once the subject feels less distressed about the image, the subject is then asked to concentrate on it while having a positive thought relating to it. It is hoped that through EMDR the subject can have more positive emotions, thoughts and behavior in the future.

Psychodynamic psychotherapy is also encompassed for use in the methods as disclosed herein and focuses on the emotional conflicts caused by the traumatic event. Through the retelling of the traumatic event to a calm, empathic, compassionate and non judgmental therapist, the patient achieves a greater sense of self-esteem, develops effective ways of thinking and coping, and more successfully deals with the intense emotions that emerge during therapy. The therapist helps the patient identify current life situations that set off traumatic memories and worsen PTSD symptoms.

Emotional Freedom Technique (often referred to as "tapping") or Thought Field Therapy, as well as is also hypnosis or hypnotherapy is encompassed for use in the methods as disclosed herein. Hypnotherapy is a legitimate therapeutic technique and if traditional psychotherapy techniques appear ineffective.

In some embodiments, the methods as disclosed herein related to administration of a xenon and/or argon composition to block reconsolidation of a traumatic memory during a psychotherapy session can be combined with biofeedback therapy. Biofeedback therapy is often aimed at changing habitual reactions to stress that can cause pain or disease. Biofeedback is particularly useful in enabling subjects to learn to control physiological processes that normally occur involuntarily, such as blood pressure, heart rate, muscle tension, and skin temperature. Many clinicians believe that some of their patients have essentially forgotten how to relax. Feedback of physical responses such as skin temperature and muscle tension provides information that aids subjects in recognizing a relaxed state. For example, one commonly used biofeedback machine detects electrical signals in muscles, and translates these signals into a form that subjects can detect (e.g., flashing bulb, beeper). Subjects can learn to relax tense muscles by learning and repeating behaviors that generate the desirable response from the machine (e.g., reduced beeping, indicative of enhanced relaxation). The three most common forms of biofeedback therapy are (1) electromyography (EMG), which measures muscle tension, (2) thermal biofeedback, which measures skin temperature, and (3) electroencephalography (EEG, neurofeedback), which measures brain wave activity. Biofeedback has been demonstrated to be useful, or suggested to be useful, for a range of medical disorders including but not limited to: anorexia nervosa and other eating disorders, anxiety and depression, asthma, autism, back pain, chronic pain, bed-wetting, incontinence, fecal incontinence, constipation, diabetes, sexual disorders, Raynaud's disease, and ADHD.

The timing of administration and therapeutically effective amount or dose of a xenon and/or argon composition used will depend on the type of administration and/or formulation of xenon and/or argon composition and the psychotherapy being used, with the particular timing and dose of the xenon and/or argon composition selected in order to ensure that a therapeutically effective level of the xenon and/or argon composition is present in the individual being treated at the time of psychotherapy. In some embodiments, the timing of administration of the xenon and/or argon composition will be at the time (e.g., during) of the psychotherapy session, and/or shortly before and/or shortly after psychotherapy. In some embodiments, the timing of administration of the xenon and/or argon composition can be a pre-treatment, e.g., before the psychotherapy, for example within about 24 hours before psychotherapy, more preferably within about 12 hours, and still more preferably within about 6 hours.

In some embodiments, the timing of administration of the xenon and/or argon composition is by self-administration by the subject, e.g., outside a psychiatrist/psychologist's office, when the subject is experiencing a spontaneous or cued re-experiencing episode. In some embodiments, the timing of administration will be soon after exposure to a traumatic event (e.g., during the event, at least 1 minute after the event, at least 2, 3, 4, 5, 6, 7, 8, 9, 10, 11, 12, 13, 14, 15, 20, 25, 30, 35, 40, 45, or 60 minutes following the event), thereby reducing traumatic memory consolidation. Thus, in some embodiments, the subject can self-administer the xenon and/or argon composition at any time of day or night (e.g., after waking from a nightmare) when the subject experiences intrusion of the traumatic memory, or upon unexpected exposure to a cue (e.g., a sight, smell, sound etc.) that reminds the subject of the trauma. Accordingly, by self-medicating with the xenon and/or argon composition, the subject is exposed to the xenon and/or argon composition in a timely manner with the memory reactivation and could block the reconsolidation of that specific traumatic memory back to the natural engram. Self-medication of the xenon and/or argon composition is advantageous as traumatic memory experiences and exposures to cues are likely to occur with higher frequency in the subject's normal everyday environment as compared to in a psychotherapy session, and can also enable effective treatment using the xenon and/or argon compositions as disclosed herein when the subject is having a high frequency of re-experiencing episodes, such as during the day or while they are asleep (e.g., in the form of nightmares). Such self-medication would allow the subject to block reconsolidation of the memory that they were dreaming about.

A "therapeutically effective amount" or "therapeutically effective dose" of the pharmacologic agent is that amount of the xenon and/or argon composition that, when administered alone or in accordance to the combination therapy, for example, in combination with or after psychotherapy of the invention, results in an improved therapeutic benefit relative to that observed with psychotherapy in the absence of administering the xenon and/or argon composition. For example, a therapeutically effective dose or amount of a xenon and/or argon composition is the amount of xenon and/or argon that reduces NMDA receptor activation or transmission in the brain relative to the level of NMDA receptor activation or transmission in the brain in the absence of administration of the xenon and/or argon. As another example, a therapeutically effective dose or amount of a xenon and/or argon compositions is the amount of xenon and/or argon that affects activity of other xenon or argon targets including, for example, cholinergic receptors, 5-HT3 receptors, TREK channels, KATP channels, among others.

The therapeutically effective dose of a xenon and/or argon composition can be administered using any medically acceptable mode of administration. Although the skilled artisan would contemplate any of the modes of administration known to one of ordinary skill, preferably the pharmacologic agent is administered according to the recommended mode of administration, for example, the mode of administration listed on the package insert of a commercially available agent.

In some embodiments of the invention, the subject is a mammal other than a human. In some embodiments, the subject is a dog, and a xenon and/or argon composition is administered to the dog in conjunction with extinction training. It is specifically contemplated herein that a xenon composition is administered before extinction training, for example, to not inhibit extinction learning. Suitable forms of extinction training include but are not limited to: training to reduce separation anxiety, extinction training to reduce anxiety associated with a particular noise (e.g., thunderstorm), training for obedience skills, and training to reduce destructive behavior, or service dog such as a war veteran dog or army or police dog who has experienced a traumatic event or is suffering from a psychiatric disorder, such as PTSD. In some embodiments, the subject is a horse, e.g., race horse. Other mammals, such as companion pets are also encompassed for treatment with a combination of a xenon and/or argon composition and psychotherapy as disclosed herein. In some embodiments, the psychotherapy uses vertical reality exposure (VRE) and/or exposes the animal subject to a stimulus that provokes a deleterious, high-anxiety response in the animal subject.

A subject undergoing treatment with the methods of the invention exhibits an improvement in one or more symptoms associated with the psychiatric disorder. For a description of the relevant symptoms, see, for example, the DSM-IV ((1994) Diagnostic and Statistical Manual of Mental Disorders (4th ed., American Psychiatric Association, Washington D.C.)), or the DSM-V ((2013) Diagnostic and Statistical Manual of Mental Disorders ($5^{th}$ edition, American Psychiatric Association, Washington, D.C.), which are each herein incorporated by reference in their entirety. The efficacy of the methods of the invention can be assessed using any clinically recognized assessment method for measuring a reduction of one or more symptoms of the particular psychiatric disorder.

A subject undergoing treatment with the methods of the invention will experience improved extinction of the deleterious, high-anxiety response that the treatment is intended to eliminate. This facilitated extinction is manifested as reduced anxiety upon exposure to a stimulus that previously prompted the deleterious, high-anxiety response. This reduction in anxiety can leads to improvement in one or more symptoms associated with the various afflictions that can be treated according to the methods of the invention. The efficacy of the methods of the invention can be assessed using any clinically recognized assessment method for measuring a reduction of one or more symptoms of the particular anxiety disorder or other afflictions that are treated. Examples of such assessment methods are described in, for example, US patent application 2006/0084659 which is incorporated herein by reference. In some embodiments, the efficacy of the methods of the present invention patient's response to a psychotherapy session in combination with the administration of a xenon and/or argon composition as disclosed herein may be assessed using any of the methods listed below, including at least one or any combination of interviews, self-report measures, therapist measures and Psychophysiological measures.

a) Interviews

The Initial Screening Questionnaire (Rothbaum et al. (1995) Am. J. Psychiatry 152(4):626-628) is a short screening instrument that is used to screen initial phone inquiries to identify those likely meeting study criteria for fear of heights.

The Structured Clinical Interview for the DSM-IV (Spitzer et al. (1987) Structured Clinical Interview for DSM III-R (SCID) (New York State Psychiatric Institute, Biometrics Research, N.Y.)) is administered to diagnose and screen for various DSM-III-R axis I disorders (e.g., schizophrenia) as well as establish co-morbid diagnoses.

The Clinical Global Improvement (CGI) Scale is a global measure of change in severity of symptoms. The scale is bipolar with 1=very much improved; 7=very much worse; and 4=no change. It has been used extensively in clinical trials for a variety of psychiatric patients (Guy (1976) ECDEU Assessment Manual for Psychotherapy (revised ed., National Institute of Mental Health, Bethesda, Md.)).

b) Self-Report Measures

The Acrophobia Questionnaire (AQ) is a short self-report questionnaire assessing specific symptoms of fear of heights. It is given weekly prior to the psychotherapy session.

The Attitude Towards Heights Questionnaire (ATHQ) is a separate self-report scale that measures slightly different aspects of avoidance, and other fear of heights related phenomena.

The Rating of Fear Questionnaire (RFQ) (Rothbaum et al. (1995) Am. J. Psychiatry 152(4):626-628) is used to further assess level of fear related to heights in general and the VRE therapy.

The State-Trait Anxiety Inventory (STAI; Spielberger et al. (1970) Manual for the State-Trait Anxiety Inventory (self-evaluation questionnaire) (Consulting Psychologists Press, Palo Alto, Calif.)) is comprised of 40 items divided evenly between state anxiety and trait anxiety. The authors reported reliability for trait anxiety was 0.81; as expected, figures were lower for state anxiety (0.40). Internal consistency ranges between 0.83 and 0.92.

The Beck Depression Inventory (BDI; Beck et al. (1961) Archives of Gen. Psych. 4:561-571) is a 21-item self-report questionnaire assessing numerous symptoms of depression. The authors report excellent split-half reliability (0.93), and correlations with clinician ratings of depression range between 0.62 and 0.66.

c) Therapist Measure

The subjective units of discomfort (SUDs) is scored by the therapist based on the participant's report during the psychotherapy session at 5 minute intervals. SUDS are rated on a 0 to 100 scale in which 0 indicates no anxiety and 100 indicates panic-level anxiety The Behavioral Avoidance Test (BAT) consists of a brief re-exposure to heights via the Virtual Reality environment, in which the therapist assesses the patient's subjective level of fear and avoidance of heights.

d) Psychophysiological Measures

Measurement of heart rate (HR) is performed and stored by a non-invasive, computer controlled monitoring device for assessment of autonomic reactivity during psychotherapy session.

Measurement of blood pressure (BP) is performed by a non-invasive, computer controlled sphygmomanometer for assessment of vascular tone and autonomic reactivity during psychotherapy session.

Measurement of galvanic skin conductance (GSR) is performed by a non-invasive, computer controlled monitoring device for assessment of autonomic fear responsively during psychotherapy session.

Xenon Compositions

Xenon gas is currently used in humans as an anesthetic with a very safe profile. Xenon has a fast "on-off" effect as it rapidly enters the brain during administration and is quickly cleared after discontinuing administration. Xenon acts through a number of mechanisms in the brain, including functioning as an antagonist of the glycine site on the NMDA receptor effectively reducing excitatory postsynaptic currents, calcium influx, and associated changes in synaptic plasticity that are critical to memory formation and reconsolidation of reactivated memories. Xenon also affects non-NMDA glutamatergic: α-amino-3 hydroxy-5-methyl-4-isoxazolepropionic acid (AMPA) receptors, two-pore domain potassium channels (TREK-1), ATP-sensitive potassium channels (KATP), several nicotinic cholinergic receptors (alpha4beta2-alpha7- and alpha4beta4 subunit containing receptors), serotonin type 3 receptors (5-HT3), strychnine-insensitive inhibitory glycine receptors (GlyRs), and tissue plasminogen activator (tPA) and plasmin. Experimental modulation of several of these targets individually has the capacity to reduce anxiety disorder symptoms. Without wishing to be bound by theory, xenon modulation of several of these targets simultaneously or near-simultaneously can contribute to the beneficial effects. Xenon also increases pro-survival factors such as BDNF and bcl2, and may inhibit pro-inflammatory cytokines such as tumor necrosis factor α and interleukin 1β.

Argon Compositions

Ar is a relatively plentiful and inexpensive noble gas present in ambient air at about 1% concentration (versus xenon which is present at about 0.0000087% in ambient air). Ar exhibits similar efficacy as xenon, and therefore, Ar can be used therapeutically as an alternative to xenon, due to the substantial cost differential between Ar and xenon.

Argon (Ar) shares number of properties with the noble gas, xenon, which we have shown to block memory consolidation and reconsolidation in a rat model of post-traumatic stress disorder (PTSD) (see IP disclosure: Meloni and Kaufman, Mar. 6, 2012, and U.S. Provisional Patent Application No. 61/735,700, filed 11 Dec. 2012). Ar confers neuroprotection in several models of brain damage and dysfunction (Jawad et al., Neurosci Lett. 460:232-6, 2009; David et al., PLoS One 2012; 7(2):e30934; David et al., Naunyn Schmiedebergs Arch Pharmacol. 386:91-5, 2013; Ryang et al., Crit Care Med. 39:1448-53, 2011; Zhuang et al., Crit Care Med. 40:1724-30, 2012).

Ar and Xe are known to interact with several proteins by binding to common sites accessible by gaseous anesthetics (Colloc'h et al., In: Chandrasekaran A (ed) Current trends in X-ray crystallography. InTech Europe, Rijeka, pp 285-308, 2012; Eckenhoff, Mol Interv. 1:258-68, 2001).

Accordingly, Ar is also effective for disrupting memories associated with PTSD, other anxiety disorders, and key events in addiction disorders, including effects of acute drug exposures, exposures to drug cues, and withdrawal effects including anhedonia. Methods disclosed herein for treatment of psychiatric disorders by administration of Ar gas alone or in combination with psychotherapy or other drug therapies. The methods of the invention encompass a variety of psychotherapy, cognitive behavioral therapy, psychodynamically oriented treatments to address psychological and psychiatric disorders including post-traumatic stress disorder (PTSD), acute stress disorder (ASD), panic disorder, obsessive compulsive disorder (OCD), generalized anxiety disorder (GAD), social anxiety disorder, phobias, and addiction disorders.

In some embodiments, an Ar composition, e.g., Ar gas is administered to an individual via inhalation either during a psychotherapy session where the recall of an aversive memory is reactivated by the patient through mental imagery, verbal recall, script recitation, virtual reality (VR) exposure therapy, or other desensitization or flooding exposure therapy, or self-administered by inhalation by the patient upon spontaneous experiencing of aversive memories, or when psychoactive drugs have been administered, or when drug cues are observed that induce drug craving, or during withdrawal anhedonia. Reactivation of consolidated memories is central to sustaining the symptoms of the psychiatric illness, and returns such memories to a labile state that is sensitive to disruption by Ar gas given the unique properties of Ar in the brain. Exposure to drug cues induces craving and relapse, and is central to sustaining drug abuse and dependence. Withdrawal anhedonia is an aversive state that is central to sustaining drug abuse and dependence.

Ar, by rapidly altering the function of brain glutamatergic and glycinergic ionotropic receptors, will block memory consolidation and reconsolidation, and will block the acute effects of some psychoactive drugs, the effects of drug cues that can precipitate relapse, and the anhedonia associated with abstinence from drug use.

Formulations of the Xenon and/or Argon Compositions

Xenon and/or argon can be administered via a gas-inhalation apparatus in the clinician's office during psychotherapy sessions. Medical-grade xenon would be packaged in cylinders at specified concentrations (% xenon in oxygen) that would prevent the possibility of asphyxiation or deep sedation. In some embodiments, the xenon and/or argon containing compositions are formulated for self-administration by the subject. For example, xenon and/or argon compositions can be administered using a hand-held canister or device packaged for self-administration by the individual outside of the clinician's office.

The xenon and/or argon compositions can be formulated as a gas (a xenon gas and/or argon gas) or as a nanoparticle (e.g., liposome) or nanosponge composition. For example, xenon gas administered to a subject (e.g., via inhalation) can contain between 0.5% to 35% xenon, 1% to 35% xenon, 2% to 35% xenon, or 5% to 35% xenon by volume, e.g., 10% to 35% xenon by volume, 10% to 35% xenon by volume, 10% to 30% xenon by volume, or 20% to 30% xenon by volume. An argon gas containing composition to be administered to a subject can contain between 10-75% argon by volume, e.g., 20-75% argon, 30-75% argon, 40-75% argon, 50-75% argon, 60-75% argon, or 65-75% argon. Xenon and/or argon gas administered to the subject can be balanced in part with oxygen gas ($O_2$) (e.g., 20% to 35% by volume, 20% to 30% by volume, or 20% to 25% by volume), nitrogen gas ($N_2$) (e.g., 25% to 75% by volume, 25% to 40% by volume, 30% to 70% by volume, 30% to 60% by volume, or 30% to 50% by volume). In some embodiments, xenon and/or argon gas administered contains 30% xenon and/or argon by volume, 30% oxygen (O2) by volume, and 40% nitrogen (N2) by volume or contains 30% xenon and/or argon by volume, 21% oxygen by volume, and 49% nitrogen by volume. Xenon and/or argon gas can also contain vaporized water (e.g., be humidified). In one embodiment, the concentration of oxygen is not lower than 21% by volume.

In some embodiments, the xenon and/or argon gas that can be used in the methods described herein, can also contain one or more additional pharmaceutical agents or additional therapeutic agents (e.g., aerosolized therapeutic agents) for treating a psychiatric disorder or decreasing one or more of the symptoms of a psychiatric disorder as disclosed herein, and include but are not limited to, norepinephrine reuptake inhibitors, for example tomoxetine, reboxetine (Edronax or Vestra), duloxetine, venlafaxine (EFFEXOR™), and milnacipran (see, for example, U.S. Pat. No. 6,028,070, the contents of which are herein incorporated by reference), and those compounds that cause release of norepinephrine, for example amphetamine, dextroamphetamine (DEXEDRINE™), pemoline (CYLERT™), and methylphenidate (RITALIN™). Another class of such pharmacologic agents are those compounds that increase the level of acetylcholine in the brain, including, for example, compounds that block its breakdown. Examples of such compounds include, but are not limited to, donepezil HCl or E2020 (ARICEPT™) and tacrine (THA, COGNEX™), which inhibit cholinesterase activity.

The xenon and/or argon compositions can also be formulated as liquids containing xenon and/or argon gas in echogenic liposomes (e.g., 10% to 100% saturation of xenon gas, 20% to 100% saturation of xenon and/or argon gas, 40% to 100% saturation of xenon and/or argon gas, 50% to 100% saturation of xenon and/or argon gas, 60% to 100% saturation of xenon and/or argon gas, 20% to 80% saturation of xenon and/or argon gas, 40% to 80% saturation of xenon and/or argon gas, or 60% to 80% saturation of xenon and/or argon gas). A single dosage of a liquid containing liposomes can be at least 20 mL to 200 mL, or 20 mL to 100 mL. In one embodiment, 1 mL of liposomes can contain 1.8 mL xenon and/or argon gas.

Liposomes that can be used in any of the methods described herein can contain a phospholipid bilayer and a core (e.g., a core of an xenon and/or argon saturated liquid or a core of xenon and/or argon gas). Non-limiting examples of such liposomes, as well as methods of their preparation, are described in Britton et al. (Circulation 122:1578-1587, 2010) and Cullis et al. (Advanced Drug Delivery Reviews 3:267-282, 1989, and all references cited therein).

The liposomes are artificial submicron vesicles that contain a phospholipid bilayer and a hydrophilic core. The phospholipid bilayer and core are ideal for incorporating a variety of gases, while maintaining the physiological inertness of its contents. Such liposomes can be used to trigger release of a gas (e.g., xenon and/or argon) from these liposomes on demand. For example, one-megahertz low-amplitude (0.18 MPa) continuous wave ultrasound can be used to release a gas (e.g., xenon and/or argon) from the liposomes, at a specific time, as they pass through the internal carotid artery, or via low intensity ultrasound focused on particular vascular beds, to specific brain areas (see, for example, Yoo et al., Neuroimage, available online, 2011).

Several methods that can be used to generate liposomes are known in the art (see, for example, Cullis et al., Advanced Drug Delivery Reviews 3:267-282, 1989). The liposomes generated can be multilamellar vesicles (MLVs), large unilamellar vesicles (LUVs), or small unilamellar vesicles (SUVs). MLVs can be generated using methods that include the addition of water to a lipid film followed by dispersal by mechanical agitation (Bangham et al., J. Mol. Biol. 13:238-252, 1965). LUVs may be generated using methods that include extrusion of preformed MLVs through filters (e.g., polycarbonate filters) with defined pore size. SUVs can be generated by sonication (Huang et al., Biochemistry 8:344-351, 1969), French press (Barenholz et al., FEBS Left. 99:210-215, 1979), and homogenization procedures (Japanese Patent No. 7934-1985).

Liposomes may be loaded with a therapeutic agent in one of several ways including, but not limited to, co-solubilization of the agent in an organic solvent with the lipid, and subsequently dispersing the mixture in aqueous buffer either after removing the solvent or by a reverse-phase procedure; co-dispersing the agent and the lipid in an aqueous buffer; or through the use of an active trapping procedure (e.g., where the agent is loaded after the liposomes have been formed).

In one non-limiting example, xenon and/or argon-encapsulating liposomes can be composed of 1,2-dipalmitoyl-sn-glycero-3-phosphocholine (DPPC), 1,2-dioleoyl-sn-glycero-3-phosphocholine (DOPC), and cholesterol at a molar ratio of 60:30:10. To make such liposomes, five milligrams of lipids can be mixed in chloroform, and the solvent evaporated with argon in a 50° C. water bath to form a thin film on a glass vial. The lipid film can then be placed under vacuum (<100 μm Hg) for a sufficient time, e.g., 4 to 6 hours to allow complete solvent removal. The dried lipid film is then hydrated (e.g., with 0.32 mol/L mannitol) and sonicated to generate liposomes. To load the liposomes with xenon and/or argon gas, the sonicated liposomes are transferred to a 2-mL glass vial with a sealed cap, and incubated with a 10 mL mixture of xenon (70% by volume)/argon (30% by volume) mixture or vice versa, (e.g., 70% by volume argon and 30% xenon). The resulting pressurized liposomes can be stored, e.g., at −70° C.

The liposomes used in the methods described herein can also contain one or more pharmaceutical agents or additional therapeutic agents for treating a psychiatric disorder or delaying the onset of one or more symptoms of a psychiatric disorder, such as agents that affect dopamine levels or metabolism (e.g., L-3,4-dihydroxyphenylalanine (L-dopa or levodopa), carbidopa, and entacapone), cholesterinase inhibitors (e.g., donepezil, rivastigmine, and galantamine), glutamate blockers (e.g., memantine HCl), monoamine oxidase inhibitors (e.g., rasagiline), and anticonvulsants (benzodiazepines, carbamazepine, vigabatrin, phenytoin, levetiracetam).

A single dosage of a xenon and/or argon composition (e.g., solid xenon and/or argon compositions, such as echogenic liposomes or nanosponges) can be 1 mg to 500 mg, 10 mg to 400 mg, 10 mg to 300 mg, 10 mg to 200 mg, 10 mg to 100 mg, 1 mg to 10 mg, 0.1 mg to 10 mg, and 0.1 mg to 5 mg.

Nanosponges that can be used in any of the methods described herein can contain a solid external core (e.g., crosslinked cyclodextrin) that contains xenon and/or argon gas. Non limiting examples of such nanoparticles, as well as methods of their preparation, are described in Cavalli et al., Int. J. Pharm. 404:254-257, 2010, and all references cited therein). For example, nanosponges may be formed by crosslinked cyclodextrin with carbonyldiimidazole. In one example, the crosslinking is performed with stirring at 80-100° C. for 4 hours. The resulting solid can be washed with water and recovered by filtration. The resulting solid can be loaded with gas by exposure to a saturated solution of gas (e.g., xenon and/or argon gas).

The nanosponges contain a solid crosslinked skeleton and a hollow core in which therapeutics gases and/or other agents can be incorporated. The solid skeleton is ideal for incorporating a variety of gases and other therapeutic agents, while maintaining the physiological inertness of its contents. Such particles can be used to trigger release of a gas (e.g., xenon and/or argon) spontaneously and on demand. For example, 2.5 MHz low amplitude (2.6 MPa) continuous wave ultrasound can be used to release a gas (e.g., xenon and/or argon) from the nanosponges (e.g., Cavalli et al., Int. J. Pharm., 2010), including low intensity ultrasound focused on particular vascular beds, to specific brain areas (Yoo et al., Neuroimage, available online, 2011).

Modes of Administration

As described herein, the xenon and/or argon compositions (e.g., a xenon and/or argon gas) can be administered to the subject during (e.g., concurrent with) and/or after psychotherapy. A single dose (e.g., a net single exposure to xenon and/or argon) can be between 0.5% to 35% xenon or between 10% to 35% xenon, a preferred single dose can be between 10% to 30% xenon and/or argon, such as 20% to 25% xenon and/or argon. A single dose can be between 10-75% argon or between 35-75% argon. For example, administration of 35% xenon and/or argon by inhalation for 1 hour at a normal ventilation rate of 6 liters/minute requires 360 liters of 35% xenon and/or argon or 126 liters of 100% xenon and/or 100% argon.

In other embodiments, a single does (e.g., a net single exposure to xenon and/or argon) can be between 0.5% to 35%, for example, 0.5% to 5%, 0.5% to 10%, 0.5% to 15%, 0.5% to 20%, 0.5% to 25%, 0.5% to 30%, or any range in between. The total amount of xenon and/or argon required for this therapy may be less as xenon and/or argon recovery systems allow xenon and/or argon recycling (e.g., Rawat and Dingley, Anesthesia and Analgesia 110:101-109, 2010).

The xenon and/or argon in the form of a gas can be chronically administered to the subject in a variety of ways, including, but not limited to, by inhalation, intraocularly, or intranasally, and such administration can provide a therapeutic effect as xenon and/or argon gas is capable of crossing the blood/brain barrier in a subject. For example, in a single administration a xenon composition (e.g., any of those described herein) can be administered over a continuous time period. In some examples of the methods described herein, a xenon and/or argon gas is administered as a bolus (e.g., by inhalation of xenon and/or argon gas).

The liquid and solid xenon and/or argon compositions (e.g., nanoparticles or nanosponges) can be administered to a subject in a variety of ways, including, but not limited to, intravenously, intraarterially, subcutaneously, intranasally, or intraocularly. For example, in a single administration, a nanoparticle (e.g., liposome) or nanosponge (e.g., any of the delivery systems described herein) containing xenon and/or argon gas can be administered to a subject one or more (e.g., two, three, or four) times during and/or after the psychotherapy session, or over a continuous time period (e.g., 5 minutes, 10 minutes, 15 minutes, 20 minutes, 25 minutes, 30 minutes, 40 minutes, 1 hour, 2 hours, 3 hours, 4 hours, 5 hours, 6 hours, 7 hours, 8 hours, 9 hours, 10 hours, 11 hours, 12 hours, 1 day, 2 days, or 3 days, or overnight (e.g., 6 to 13 hours)) during or after the psychotherapy session, or can be administered as a bolus (e.g., as a liquid to be injected or administered to the eye) during or after the psychotherapy session. In some embodiments of the methods described herein, echogenic waves are used to disrupt the nanoparticles (e.g. echogenic liposomes) or nanosponges containing xenon and/or argon gas in one or more tissues (e.g., brain tissue or spinal cord) in the subject.

During a prolonged period of psychotherapy treatment, e.g., during a period of daily therapy sessions, a xenon and/or argon composition can be administered to the subject once a day, twice a day, three times a day, four times a day, once a week, twice a week, three times a week, four times a week, five times a week, six times a week, seven times a week, once every two weeks, twice every two weeks, three times every two week, four times every two weeks, once a month, twice a month, three times a month, four times a month, five times a month, six times a month, seven times a month, or 8 times a month). As described herein, each administration can take place over a continuous period of time or the administration can be provided as a bolus.

In any of the methods described herein, the frequency, duration, and or dosage of administration of a xenon and/or argon composition can be dependent on the occurrence of the psychotherapy sessions, (e.g., as the psychotherapy sessions occur, e.g., once during and/or after the psychotherapy session, or multiple times during and/or after the psychotherapy session, or continuously during and/or after the psychotherapy session). Such variation of the frequency, duration, and/or dosage of single administrations of the xenon and/or argon composition can be performed by a health care professional based on the subject's ability to recall traumatic events in the psychotherapy session. For example, the health care professional can alter the frequency, duration, and/or dosage of single administrations of the xenon and/or argon gas or xenon and/or argon composition during and/or after the psychotherapy session following the assessment of the severity, frequency, or duration of one or more symptoms of the psychiatric disorder in the subject, and/or recall by the subject of the anxiety triggering memory. That is, the route, frequency of duration and or dosage of administration can be varied by one of skill in the art. Individual administrations do not have to take place over a common continuous time period. For example, at least one single administration can take place over a period of 1 hour and at least one additional administration can take place over a period of 8 hours. For example, 35% xenon and/or argon administered as inhalation therapy at normal breathing rates for 1 hour (360 liters total volume at a minute volume of 6 liters/min for a healthy adult) would require 126 liters of xenon and/or argon. Lower xenon and/or argon doses (e.g., 10%) would require 36 liters per hour of inhalation therapy. This xenon and/or argon can be recovered and reused (e.g., Rawat and Dingley, Anesthesia and Analgesia 110:101-109, 2010), so it is possible that the total amount of xenon and/or argon to support an hour of inhalational therapy can be less than 126 or 36 liters.

Xenon Composition Delivery Systems

Figure 2:
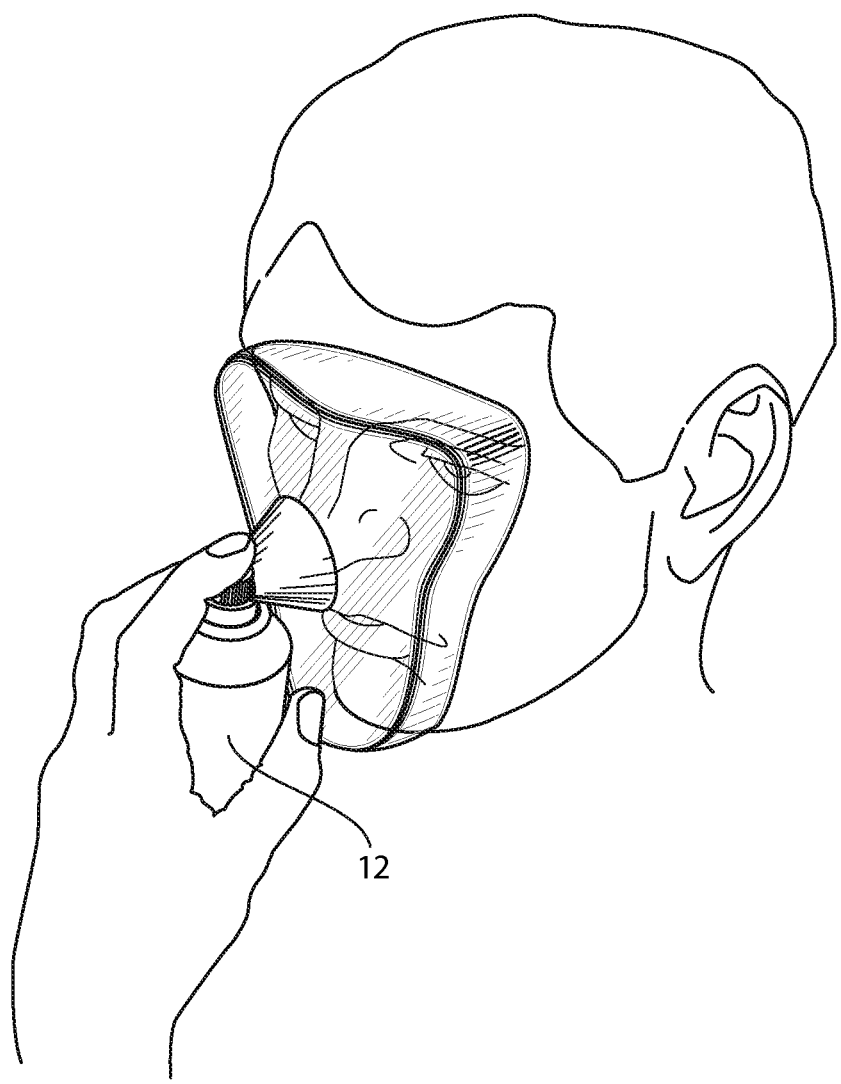
FIG. 2 is a picture of a face mask and a portable xenon and/or argon gas canister that can be used to administer xenon gas.

A xenon and/or argon gas (e.g., any of the xenon and/or argon gas compositions described herein) can be administered to the subject through the use of self-contained breathing apparatus (e.g., a mouthpiece, face mask, or other hand-held device, acontinuous positive airway pressure (CPAP) device, and/or a nose mask) or a nebulizer (inhaler). Non-limiting examples of mouthpieces or face masks that can be used to administer a xenon and/or argon gas are described in U.S. Pat. Nos. 6,125,844; 6,247,470; 6,981, 502; 7,870,860; 7,775,208; 7,000,611; 6,981,502; 6,779, 521; 7,866,320; 6,779,521; 5,413,095; 6,408,853; 5,348, 000; 6,715,485; 5,243,971; and 6,112,746; and U.S. Patent Application Nos. 2005/0205098, 2008/0223369; 2004/ 030639 (each of the listed patents and patent application publications are herein incorporated by reference in their entirety). FIG. 2 shows a non-limiting example of a face mask and a portable xenon and/or argon gas canister that can be used in the methods described herein.

Figure 3:
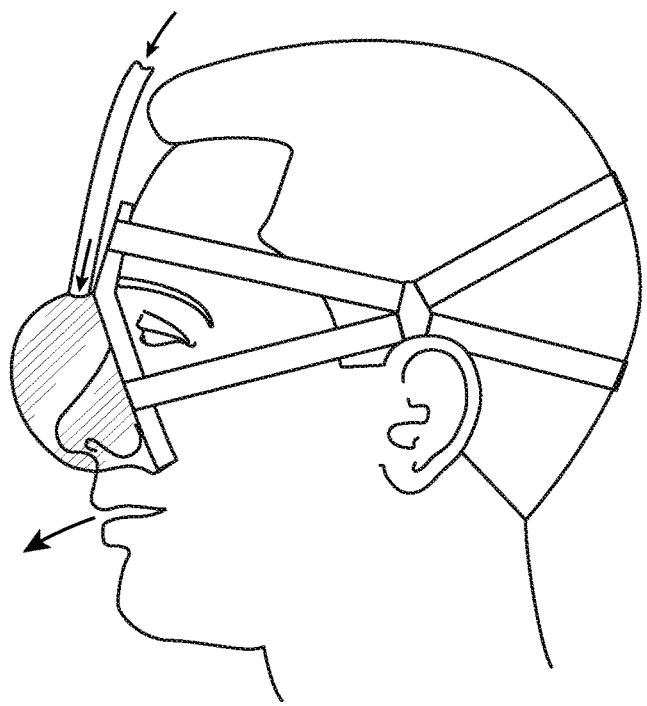
FIG. 3 is a picture of a nose mask that can be used to administer xenon and/or argon gas.

Non-limiting examples of nose masks that can be used to administer xenon and/or argon gas are described in U.S. Pat. Nos. 4,354,488; 7,207,333; 6,439,235; 6,807,966; 4,660, 555; 4,742,824; 6,595,215; and 4,721,060, and U.S. Patent Application Publication Nos. 2010/0242959 and 2004/ 030639 (each of the listed patents and patent application publications are herein incorporated by reference in their entirety). FIG. 3 shows a non-limiting example of a nose mask that can be used in the methods described herein.

When using such masks, typical dosages of xenon and/or argon gas range from 0.25 to 1.0 liters per hour of any of the xenon and/or argon gas compositions described herein.

Figure 4:
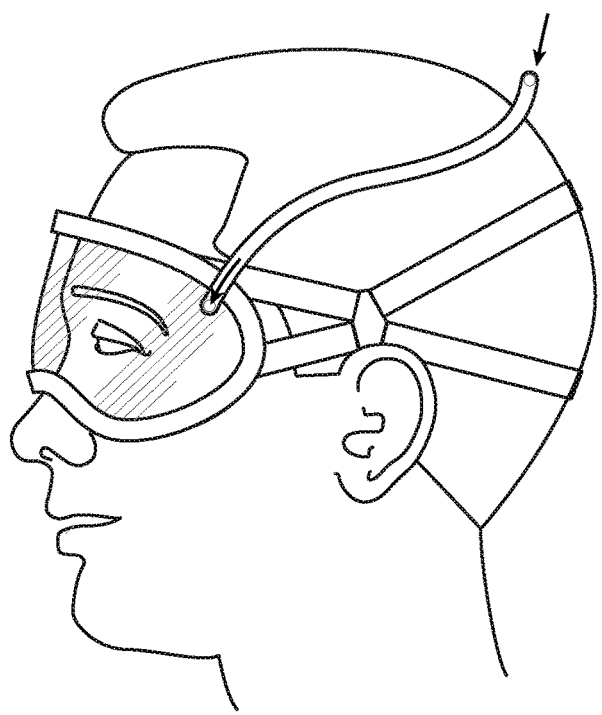
FIG. 4 is a picture of sealable goggles that can be used to administer xenon and/or argon gas.
Figure 5:
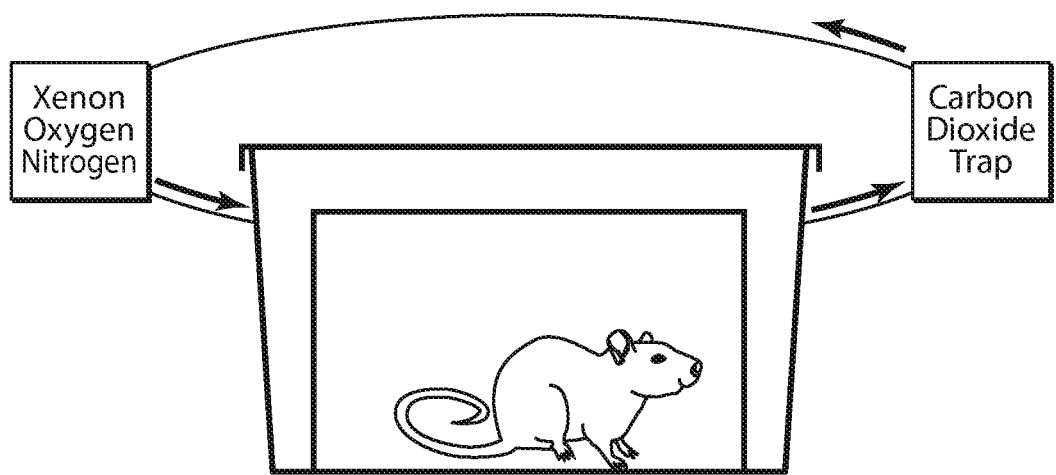
FIG. 5 is a diagram of an apparatus for treating rodents with xenon and/or argon gas.

Xenon and/or argon gas compositions can also be administered to the subject through the use of self-contained goggles (e.g., goggles that can be worn one or more hours (e.g., at least two, three, four, five, or six hours) or overnight (e.g., between 5-13 hours) (see, for example, FIG. 4). The goggles can also be equipped with a liquid crystal display (LCD) screen and/or audio speakers (which allow the subject to watch a movie or images and/or listen to sound while wearing the goggles). A tank (e.g., a portable tank) containing a xenon and/or argon gas composition can be provided for use with the self-contained breathing apparatus or the self-contained goggles.

For example, a system for performing the methods described herein can contain sealable goggles that cover a subject's eyes that contain at least one opening that allows xenon and/or argon gas to enter the space enclosed by the goggles and a source of xenon and/or argon gas (e.g., a tank of xenon and/or argon gas), where the sealable goggles and the xenon and/or argon gas are connected to each other. The systems provided can further include tubing that connects the sealable goggles to the source of xenon and/or argon gas. The sealable goggles can further contain a strap that allows the sealable goggles to be positioned (e.g., securely positioned) over the subject's eyes. When using such goggles, the xenon gas composition can contain up to 100% xenon and/or argon, with the rest of the gas being either air or comprising a mixture of O2 and N2 (as described herein). Typical application pressures of a xenon and/or argon gas composition administered to the eyes range from 5 to 10 mbar, e.g., 5 to 10 mbar, which results in a blood level of xenon and/or argon of about 100 to 200 nL xenon/mL blood or 100-200 argon/mL blood. A dose that may be administered to the subject using the goggles is 5-10 mbar xenon and/or argon gas per one hour.

In any of the methods described herein, a subject can be further administered one or more additional pharmaceutical agents or therapeutic agents for treating a psychiatric disorder or for decreasing the severity of one or more symptoms of a psychiatric disorder, for example, one such class of pharmacologic agents contemplated herein comprises compounds that increase the level of norepinephrine in the brain. Such compounds include those acting as norepinephrine reuptake inhibitors, for example tomoxetine, reboxetine (Edronax or Vestra), duloxetine, venlafaxine (EFFEXOR™), and milnacipran (see, for example, U.S. Pat.

No. 6,028,070, the contents of which are herein incorporated by reference), and those compounds that cause release of norepinephrine, for example amphetamine, dextroamphetamine (DEXEDRINE™), pemoline (CYLERT™), and methylphenidate (RITALIN™). Another class of such pharmacologic agents are those compounds that increase the level of acetylcholine in the brain, including, for example, compounds that block its breakdown. Examples of such compounds include, but are not limited to, donepezil HCl or E2020 (ARICEPT™) and tacrine (THA, COGNEX™) which inhibit cholinesterase activity. In some embodiments, an additional compound is administered to the subject during the psychotherapy session or during or before or after administration of the xenon and/or argon composition. In some embodiments, the additional compound is 3,4-methylenedioxy-N-methylamphetamine (MDMA), as disclosed in Doblin R, J Psychoactive Drugs. 2002 April-June; 34(2): 185-94 "A clinical plan for MDMA (Ecstasy) in the treatment of posttraumatic stress disorder (PTSD): partnering with the FDA". In some embodiments, a xenon and/or argon composition can be administered in combination with MDMA according to the methods as disclosed herein.

In some embodiments, an additional compound is administered to the subject during the psychotherapy session or during or before or after administration of the xenon and/or argon composition is a pharmacologic agent that reduces N-methyl-D-aspartate (NMDA) receptor activation or transmission (cation flow) in the brain without adverse consequences such as neurotoxic effects. Such reduced NMDA receptor transmission can be measured by a variety of methods known to the skilled artisan. Other methods include electrophysiological and chemical methods (see Mothet et al. (2000) Proc. Natl. Acad. Sci. USA 97(9):4926-4931). Neurotoxicity can be measured by, for example, the cultured cerebellar granule neuron system described in Boje et al. (1993) Brain Res. 603(2):207-214.

In some embodiments, an additional compound is administered to the subject during the psychotherapy session or during or before or after administration of the xenon composition is a FAAH inhibitor, which have been proposed as potential therapeutics for treatment of a wide variety of clinical indications including anxiety disorders, neuropathic pain, acute pain, chronic pain, emesis, anxiety, feeding behavior, movement disorders, glaucoma, sleep disorders, brain injury, and cardiovascular disease (U.S. Pat. No. 6,699,682, and U.S. Patent Application Nos. 2004/0127518, 2005/0131032, 2003/0092734, 2002/0188009).

In addition, N-methyl-D-aspartate (NMDA) receptor agonists have been shown to enhance extinction when administered either systemically or infused directly into the amygdala (as reviewed in Davis et al. (2005), Current Directions in Psychological Science, 14(4): 214-219). In pending U.S. Patent Application No. 2005/0096396, Davis et al. describe use of the partial NMDA receptor agonist D-cycloserine (DCS) to facilitate extinction in rats, and subsequently in humans to facilitate extinction in conjunction with psychotherapy for treatment of phobic disorders.

In some embodiments, the present invention contemplates use of xenon and/or argon is a "partial antagonist" or "competitive antagonist" of the glycine site on the NMDA receptor. Xenon and/or argon as used herein does the exact opposite of agents like d-cycloserine (DCS), which functions as an NMDA agonist. Other NMDA agonists include, but are not limited to, compounds that act at the glycine modulatory site of the NMDA receptor (see Yamakura and Shimoji (1999) Prog. Neurobiol. 59(3):279-298), including D-cycloserine (DCS) (see U.S. Pat. Nos. 5,061,721 and 5,260,324), D-serine, and 1-aminocyclopropane-carboxylic acid (ACPC) (see U.S. Pat. Nos. 5,086,072 and 5,428,069, herein incorporated by reference). Other pharmacologic agents that act as partial NMDA antagonists, including polyamines such as spermine and spermidine, are also suitable for use in the methods of the present invention (Yamakura and Shimoji (1999) Prog. Neurobiol. 59(3):279-298). Spermine can functions as a mixed agonist/antagonist.

In some embodiments, a preferred time of administration is within about 3-8 hours before psychotherapy. For this pharmacologic agent, dosage levels include a low dose level of between about 30-100 mg, and a high dose level of between about 400-500 mg. In one embodiment, D-cycloserine is administered in combination with D-alanine to minimize any potential gastrointestinal effects of this pharmacologic agent. See U.S. Pat. Nos. 5,061,721 and 5,260,324, herein incorporated by reference.

The one or more additional pharmaceutical agents can be administered in a dosage of 1 mg to 500 mg, 1 mg to 400 mg, 1 mg to 300 mg, 1 mg to 200 mg, 1 mg to 100 mg, 0.1 to 50 mg, 0.1 mg to 20 mg, 0.1 mg to 10 mg, or 0.1 mg to 5 mg. The additional pharmaceutical agents can be administered at the same time (e.g., coincident with the xenon and/or argon gas or xenon and/or argon composition (in the same dosage form or as a separate dosage form). The additional pharmaceutical agent can be administered prior to or after at least one dose of a xenon and/or argon gas or a xenon and/or argon composition.

The present invention may be as defined in any one of the following numbered paragraphs.

1. A method for treating a subject with a psychiatric disorder comprising administering to the subject a therapeutically effective amount of a xenon and/or argon composition in combination with a session of psychotherapy, wherein during the session of psychotherapy the subject is exposed to a stimulus and trained to develop an altered response to said stimulus.

2. The method of paragraph 1, wherein the psychiatric disorder is selected from the group consisting of a fear and/or anxiety disorder, an addictive disorder, a mood disorder.

3. The method of paragraph 2, wherein the fear and anxiety disorder is selected from the group consisting of: a panic disorder, a phobia, post-traumatic stress disorder (PTSD), social anxiety disorder, obsessive-compulsive disorder (OCD).

4. The methods of paragraph 1, wherein administration of the xenon and/or argon composition is during and/or after the session of psychotherapy.

5. An improved psychotherapy method comprising administering to a subject in need thereof a therapeutically effective amount of a xenon and/or argon composition in combination with a session of psychotherapy, wherein the xenon and/or argon composition facilities the extinction of a high-anxiety response during the session of psychotherapy, wherein the subject is exposed to a stimulus which provokes a high-anxiety response in the subject during the session of psychotherapy.

6. A method for blocking the reconsolidation of re-activated, traumatic memories elicited spontaneously or through the psychotherapy session comprising:

a. administering to the subject a xenon and/or argon composition; and b. exposing the subject to stimuli that remind the subject of the event that produces a high-anxiety response or asking the subject to recall or remember details of the traumatic event, phobia, or specific fear.

7. The methods of paragraph 5 or 6, wherein administration of the xenon and/or argon composition is during and/or after the session of psychotherapy.

8. The method of paragraph 5 or 6, wherein the psychotherapy session is performed within one hour before the administration of the xenon and/or argon composition.

9. The method of paragraph 5 or 6, wherein the psychotherapy session is performed within two hour before the administration of the xenon and/or argon composition.

10. The method of any of paragraphs 6 to 9, wherein the psychotherapy session comprises psychotherapy.

11. The method of any of paragraphs 6 to 10, wherein the psychotherapy session is selected from the group consisting of: exposure-based psychotherapy, cognitive psychotherapy, and psycho-dynamically oriented psychotherapy.

12. A method for blocking the reconsolidation of re-activated, traumatic memories elicited spontaneously in a subject comprising the subject self-administering a therapeutically effective amount of a xenon and/or argon composition after the subject has experienced a memory of a traumatic event, phobia or specific fear, or been exposed to a specific event that produces a high-anxiety response.

13. The method of any of paragraphs 5 to 12, wherein the high anxiety response exacerbates a symptom of a medical disorder selected from the group consisting of: anxiety disorders, chronic pain, neuropathic pain, insomnia and erectile dysfunction.

14. The method of paragraph 13, wherein the medical disorder is a fear or anxiety disorder.

15. The method of paragraph 14, wherein a fear or anxiety disorder is selected from the group consisting of: a panic disorder, a phobia, post-traumatic stress disorder (PTSD), social anxiety disorder, obsessive-compulsive disorder (OCD).

16. The method of paragraph 14, wherein a fear or anxiety disorder is post-traumatic stress disorder (PTSD).

17. The method of paragraph 5 or 6, wherein the psychotherapy session extinguishes a deleterious, high anxiety response that contributes to a medical disorder selected from the group consisting of: chronic pain, neuropathic pain, insomnia and erectile dysfunction.

18. The method of paragraph 5 or 6, wherein the psychotherapy session comprises:
a. exposing the subject to a stimulus which causes anxiety associated with a medical condition or the post-traumatic stress disorder (PTSD),
b. administering to the subject a therapeutically effective amount of a xenon and/or argon composition during and/or after the subject is exposed to the stimulus.

19. The method of any of paragraphs 1 to 18, wherein the subject has been diagnosed with a fear or anxiety disorder.

20. The method of any of paragraphs 1 to 18, wherein the subject has been diagnosed with post-traumatic stress disorder (PTSD).

21. The method of any of paragraphs 1 to 20, wherein the subject is a human subject.

22. The method of any of paragraphs 1 to 20, wherein the subject is a domestic animal.

23. The method of paragraph 22, wherein the domestic animal is a dog.

24. The method of any of paragraphs 1 to 23, wherein the argon composition comprises argon gas.

25. The method of any of paragraphs 1 to 24, wherein the argon gas is administered at a concentration of 10% to 35% by volume in 21% by volume oxygen gas and a balance of nitrogen gas.

26. The method of any of paragraphs 1 to 25, wherein the xenon and/or argon gas is administered by inhalation, intraocularly, or intranasally.

27. The method of any of paragraphs 1 to 26, wherein the xenon and/or argon composition comprises a nanoparticle or nanosponge.

28. The method of paragraph 27, wherein the nanoparticle or nanosponge is administered intravenously, intraarterially, intramuscularly, subcutaneously, intranasally, or intracranially.

29. The method of any of paragraphs 1 to 28, wherein the xenon and/or argon composition is administered to the subject over a continuous period of time during and/or after the psychotherapy session.

30. The method of paragraph 29, wherein the continuous period of time is at least 15 minutes.

31. The method of any of paragraphs 1 to 30, wherein the subject is administered the xenon and/or argon composition at least one time during and/or after the psychotherapy session.

32. The method of any of paragraphs 1 to 31, wherein the subject is administered the xenon and/or argon composition at least one time during and/or after the psychotherapy session.

33. The method of any of paragraphs 1 to 32, wherein the subject is administered the xenon and/or argon composition at multiple times during and/or after the psychotherapy session.

34. The method of any of paragraphs 1 to 33, wherein the subject is administered additional compounds for treatment of the fear or anxiety disorder.

35. The method of paragraph 34, wherein the additional compound is 3,4-methylenedioxy-N-methylamphetamine (MDMA).

36. The method of any of paragraphs 1 to 35, wherein the administration of the xenon and/or argon compound to the subject is self-administration.

37. The method of paragraph 12, wherein the subject experiences a memory of a traumatic event, phobia or specific fear while the subject is asleep.

38. The method of any of paragraphs 1 to 36, wherein the subject is exposed to stimuli that remind the subject of an event that produces a high-anxiety response or asked to recall or remember details of the traumatic event, phobia, or specific fear while the subject is hypnotized.

39. A system for administering a xenon and/or argon gas to the eye of a subject, comprising:
a. sealable goggles that cover a subject's eyes that comprise at least one opening that allows xenon and/or argon gas to enter the space enclosed by the goggles; and
b. a source of xenon and/or argon gas, wherein the sealable goggles and the xenon and/or argon gas are connected to each other 40. The system of paragraph 39, further comprises tubing that connects the sealable goggles to the source of xenon and/or argon gas.

41. The system of paragraph 39, wherein the sealable goggles further comprise a strap for securing the goggles over the subject's eyes.

42. The system of paragraph 39, wherein the sealable goggles further comprise a display screen or a speaker, or both.

43. The method of paragraph 1, 5, 6 and 12, wherein the argon composition further comprises xenon or wherein the xenon composition further comprises argon.

44. The system of paragraph 39, further comprising administering xenon and/or argon gas to the eye of the subject, wherein the xenon gas can enter the space enclosed by the goggles.

45. The method or system of any one of claims 1-44, wherein the psychiatric disorder is not psychoactive substance use and/or anxiety disorders.

46. A method for preventing or reducing trauma memory consolidation in a subject, the method comprising administering to a subject in need thereof a therapeutically effective amount of a xenon and/or argon composition during or following a traumatic event, thereby preventing or reducing trauma memory consolidation in the subject.

47. The method of paragraph 46, wherein the psychiatric disorder is selected from the group consisting of a fear and/or anxiety disorder, an addictive disorder, a mood disorder.

48. The method of paragraph 47, wherein the fear and anxiety disorder is selected from the group consisting of: a panic disorder, a phobia, post-traumatic stress disorder (PTSD), social anxiety disorder, obsessive-compulsive disorder (OCD).

49. The methods of paragraph 47, wherein administration of the xenon and/or argon composition is during and/or after the session of psychotherapy.

50. Use of a xenon and/or argon composition alone or in combination with psychotherapy for the treatment of a subject having a psychiatric disorder.

51. The use of paragraph 50, wherein the psychiatric disorder is a fear and/or anxiety disorder, an addictive disorder, or a mood disorder.

52. Use of a xenon and/or argon composition to facilitate the extinction of a high-anxiety response during a session of psychotherapy, wherein the subject is exposed to a stimulus which provokes a high-anxiety response in the subject during the session of psychotherapy.

53. Use of a xenon and/or argon composition for blocking the reconsolidation of re-activated, traumatic memories elicited spontaneously or through a psychotherapy session.

54. The use of paragraph 53, wherein the subject is exposed to stimuli that reminds the subject of the event that produces a high-anxiety response or asking the subject to recall or remember details of the traumatic event, phobia, or specific fear.

55. Use of a self-administered xenon and/or argon composition for blocking the reconsolidation of re-activated traumatic memories elicited spontaneously in a subject after the subject has experienced a memory of a traumatic event, phobia or specific fear, or been exposed to a specific event that produces a high-anxiety response.

56. Use of a xenon and/or argon composition for preventing or reducing trauma memory consolidation in a subject.

EXAMPLES

Methods:

An illustration of the methodology used for training and testing rats in the conditioned freezing paradigm is shown in FIG. 1 (see also Johansen et al., Cell, 2011, 147; 509-524). Male Sprague-Dawley rats (350-375 g) were housed for at least one week before the experiment. On the training day, rats were placed into a conditioning chamber, housed within a sound-attenuating cabinet (Med Associates, Georgia, Vt.), for 2 min before the onset of the conditioned stimulus (CS). The CS was a tone (5 kHz, 75 dB) that lasted for 30 s. The last 2 s of the CS were paired with a continuous foot shock (0.6 mA, the unconditioned stimulus (US)). Rats received two presentations of the CS+US (tone plus shock). After additional 30 s in the chamber, rats were randomly divided into two groups (n=4/group) and immediately placed in either the Air or xenon-exposure chambers. After 24-h of air or xenon (25%) exposure, rats were tested for retention of conditioned fear using conditioned freezing as a measure of fear. For the test, rats were placed into a different context and, 2 min later, were exposed to the tone CS (5 kHz, 75 dB) for 60 s. Freezing scores were calculated as the percentage of the total duration that the rat remained immobile (frozen) other than breathing during the first 2 min (freezing to context) and during presentation of the CS (freezing to tone). Rats were then returned to the main animal holding room (i.e. no more air or xenon exposure took place) and were retested 1 and 2 weeks later (re-test and $3^{rd}$ test) as described above. As shown in FIGS. 1B & C, xenon exposure reduced levels of conditioned freezing to both the context and tone (CS) on all test days, indicating that xenon was effective in blocking the formation of fear memory in rats.

Example 1

Effects of Xenon on Consolidation and Reconsolidation of Fear Memory

Newly formed memories, including traumatic memories, are stabilized over several hours after the acquisition for long-term storage. This process, termed consolidation, critically depends on the permanence of acquisition-induced synaptic modifications in the corresponding neural circuits and is NMDA-receptor dependent. Once retrieved, consolidated memory enters a labile state again and should be reconsolidated, or it will be diminished or lost (see Debiec, 2012). To explore the effects of xenon exposure on post-retrieval memory reconsolidation, the inventors trained and tested male Sprague-Dawley rats in the conditioned freezing paradigm described in the methods section above. As shown in FIG. 1, this training procedure resulted in stable CS-induced conditioned freezing responses in Air-treated rats (i.e. the control group), which did not exhibit any decreases following two additional reactivation trials 1 and 2 weeks after an initial fear memory test.

Immediately after the fear memory test (24 h post-conditioning), where animals are subjected to context and CS (tone) exposure previously paired with shock (on the training day), rats were placed in either the Air or xenon (25%) exposure chambers for 1 hr. Rats were then tested for conditioned freezing 48 hours later. The inventors demonstrate that xenon treatment interferes with memory reconsolidation processes and reduces the expression of conditioned freezing to both the context and the tone cue.

Figure 1D:
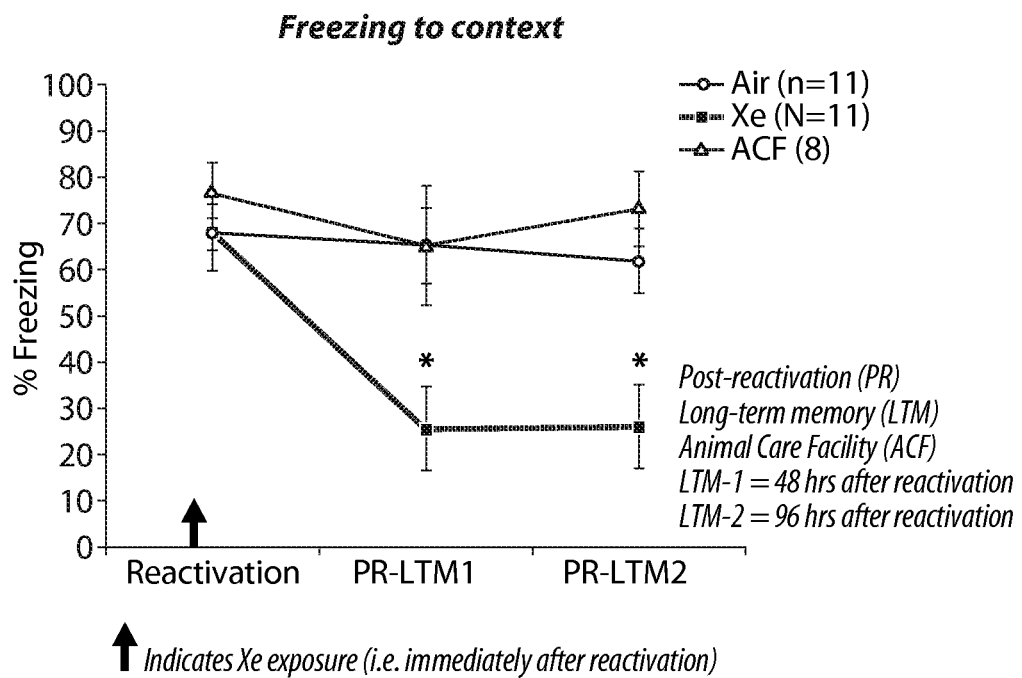
Figure 1E:
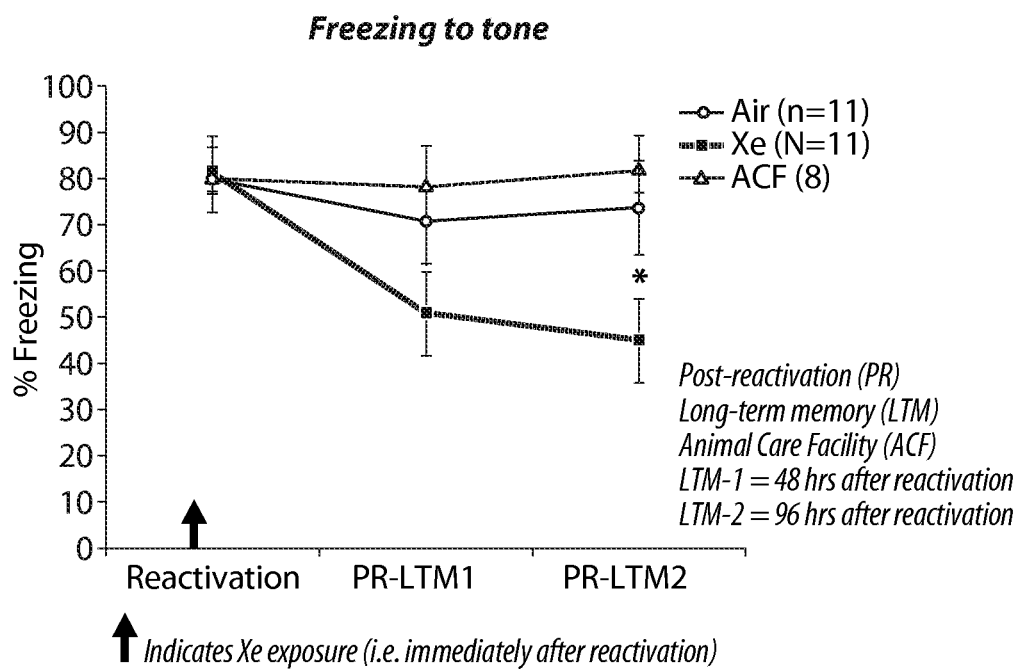
Figure 1F:
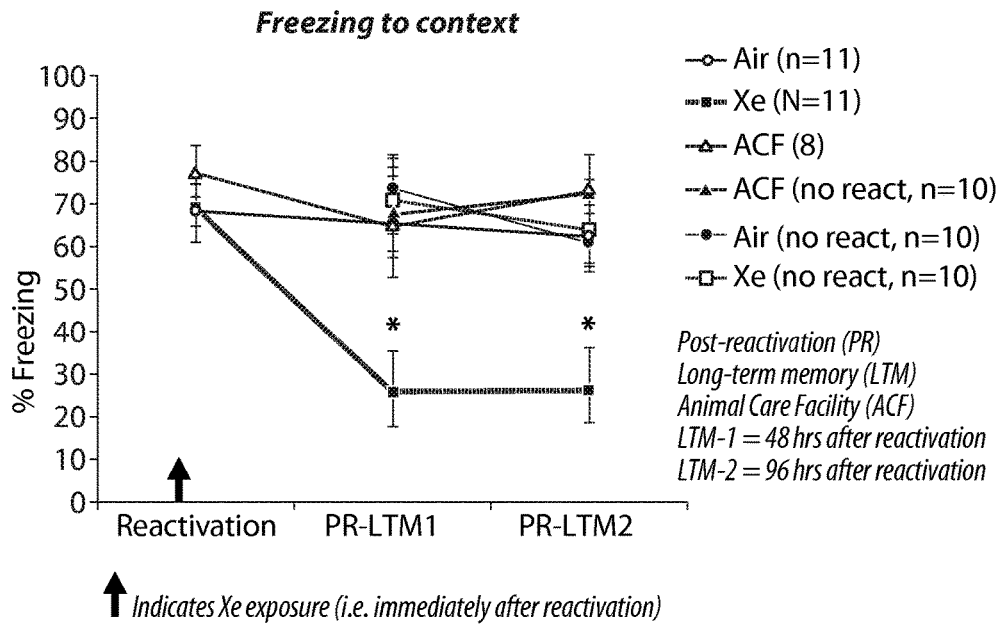
Figure 1G:
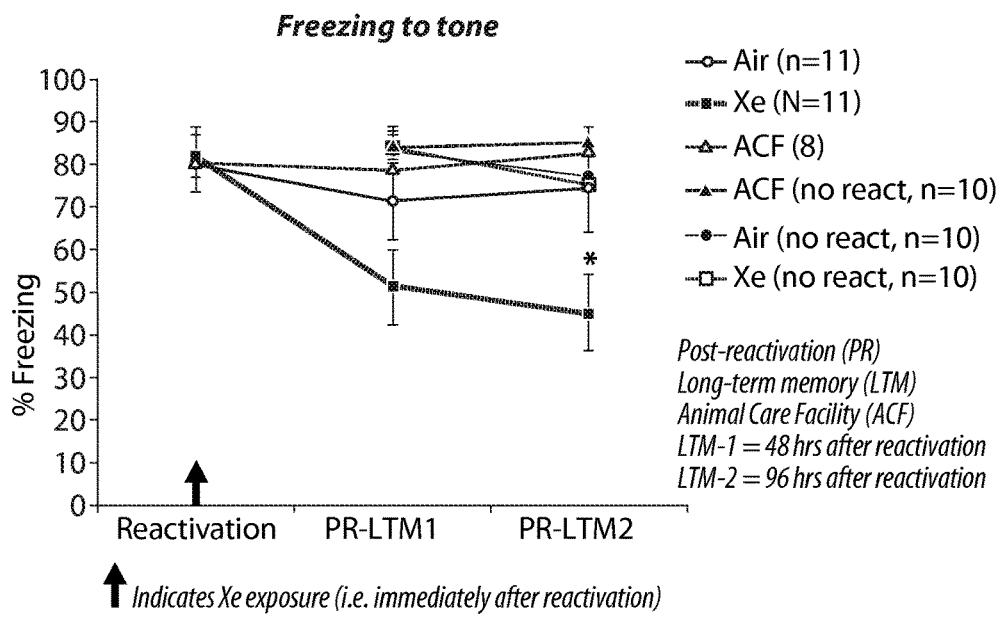

In a separate experiment, animals were trained for fear conditioning as described above and tested for freezing 24 h later (reactivation). Rats were divided into 3 different groups and exposed to normal room air (ACF-housed and Air-treated groups) or Xe (25%) for one hour. 48 hours later, rats were re-tested for freezing to both the conditioning context and cue. Xe-treated rats showed significantly less freezing tested on this day (PR-LTM1) or after another 48 hours (PR-LTM2) indicating that Xe blocked reconsolidation of fear memory (FIGS. 1D & 1E). Additionally, animals that were exposed to Xe (25%), but did not receive a reactivation test (no react group, FIGS. 1F & 1G), showed no reduction in freezing to either the context or tone (FIGS. 1F & 1G, respectively), indicating the necessity of pairing xenon exposure with the reactivation of the fear memory in order to effect a reduction in freezing.

Such an effect demonstrated herein provides preclinical support for use of xenon and/or argon treatment as an adjunct to psychotherapy for psychiatric disorders, and that that xenon therapy may be efficacious in the treatment of psychiatric disorders such as but not limited to PTSD.

REFERENCES

All references cited in the specification and Examples section are incorporated herein in their entirety by reference.

Debiec, J., Memory Reconsolidation Processes and Post-traumatic Stress Disorder: Promises and Challenges of Translational Research. Biol Psychiatry, 2012; 71; 284-285

Johansen et al., Molecular Mechanisms of Fear Learning and Memory, 2011; Cell; 147; 509-524.

The invention claimed is:

1. A method for treating a subject comprising administering to a subject having an addictive disorder or a fear and/or anxiety disorder a xenon composition consisting essentially of 0.5-35% xenon, in combination with a session of psychotherapy, wherein during the session of psychotherapy the subject is exposed to a stimulus and trained to develop an altered response to said stimulus.

2. The method of claim 1, wherein the fear and/or anxiety disorder is selected from the group consisting of: a panic disorder, a phobia, post-traumatic stress disorder (PTSD), social anxiety disorder, and obsessive-compulsive disorder (OCD).

3. The method of claim 1, wherein administration of the xenon composition is during and/or after the session of psychotherapy.

4. A method for blocking the reconsolidation of re-activated, traumatic memories elicited spontaneously or through a psychotherapy session comprising:
   a. administering to the subject a xenon composition, wherein the xenon composition consists essentially of 0.5-35% xenon; and
   b. exposing the subject to stimuli that remind the subject of the event that produces a high-anxiety response or asking the subject to recall or remember details of the traumatic event, phobia, or specific fear.

5. The method of claim 4, wherein administration of the xenon composition is during and/or after the session of psychotherapy.

6. The method of claim 4, wherein the psychotherapy session is performed within one hour before the administration of the xenon composition.

7. The method of claim 4, wherein the psychotherapy session is performed within two hours before the administration of the xenon composition.

8. The method claim 4, wherein the psychotherapy session is selected from the group consisting of: exposure-based psychotherapy, cognitive psychotherapy, and psycho-dynamically oriented psychotherapy.

9. The method of claim 1, wherein the xenon composition further comprises oxygen, nitrogen and/or water vapor.

10. The method of claim 9, wherein the xenon composition further comprises 20-25% oxygen.

* * * * *

UNITED STATES PATENT AND TRADEMARK OFFICE
CERTIFICATE OF CORRECTION

| | |
|---|---|
| PATENT NO. | : 9,737,562 B2 |
| APPLICATION NO. | : 14/650479 |
| DATED | : August 22, 2017 |
| INVENTOR(S) | : Meloni et al. |

It is certified that error appears in the above-identified patent and that said Letters Patent is hereby corrected as shown below:

In the Specification

At Column 1, Line 17:
Insert the following heading and paragraph:
--GOVERNMENT SUPPORT
This invention was made with government support under NS080073 awarded by the National Institutes of Health. The government has certain rights in the invention.--

Signed and Sealed this
Ninth Day of May, 2023

Katherine Kelly Vidal
*Director of the United States Patent and Trademark Office*